United States Patent [19]

Freund et al.

[11] Patent Number: 5,080,708
[45] Date of Patent: Jan. 14, 1992

[54] ISOXAZOLE(ISOTHIAZOLE)-5-CARBOXA-MIDES

[75] Inventors: Wolfgang Freund, Neustadt; Thomas Kuekenhoehner, Frankenthal; Gerhard Hamprecht, Weinheim; Bruno Wuerzer, Otterstadt; Karl-Otto Westphalen, Speyer; Norbert Meyer, Ladenburg; Hans Theobald, Limburgerhof, all of Fed. Rep. of Germany

[73] Assignee: BASF Aktiengesellschaft, Ludwigshafen, Fed. Rep. of Germany

[21] Appl. No.: 337,640

[22] Filed: Apr. 13, 1989

[30] Foreign Application Priority Data

Apr. 13, 1988 [DE] Fed. Rep. of Germany ....... 3812225

[51] Int. Cl.$^5$ .................... A01N 43/80; A01N 43/76; A01N 43/48; C07D 263/34; C07D 263/36; C07D 261/04; C07D 413/04; C07D 413/12; C07D 413/14

[52] U.S. Cl. .......................... 71/88; 71/86; 71/90; 71/92; 71/94; 71/95; 544/64; 544/69; 544/137; 544/225; 544/229; 544/243; 544/328; 544/331; 546/5; 546/14; 546/22; 546/209; 546/275; 548/104; 548/110; 548/119; 548/238; 548/243; 548/248

[58] Field of Search ............... 548/238, 243, 248, 110, 548/119, 104; 71/88, 90, 92, 94, 95, 86; 544/137, 331, 64, 69, 225, 229, 243, 328; 546/209, 275, 5, 14, 22

[56] References Cited

PUBLICATIONS

Nesi et al., J. Chem. Soc. Perkin Trans. I p. 1005 (1987).
Camparini et al., J. Chem. Soc. Perkin, Perkin Trans. I 1982, p. 2391.
Camparini et al., J. Heterocyclic Chem. vol. 22, (1985) p. 1561.
Adams et al., J. Chem. Soc. (1959), p. 3061.

Primary Examiner—John M. Ford
Assistant Examiner—E. Bernhardt
Attorney, Agent, or Firm—Oblon, Spivak, McClelland, Maier & Neustadt

[57] ABSTRACT

Isoxazole(isothiazole)-5-carboxamides of the formula where
X is oxygen or sulfur,
$R^1$ is hydrogen, substituted or unsubstituted alkyl, alkoxy, substituted or unsubstituted cycloalkyl, a 5- or 6-membered heterocyclic radical having one or two heteroatoms selected from the group consisting of oxygen, sulfur and nitrogen, and which may be substituted, or substituted or unsubstituted phenyl, or
$R^2$ is formyl, 4,5-dihydrooxazol-2-yl or a radical of the formula COYR$^5$ or CONR$^6$R$^7$, where
Y is oxygen or sulfur,
$R^5$ is
hydrogen, substituted or unsubstituted alkyl, substituted or unsubstituted alkenyl, haloalkenyl, substituted or unsubstituted alkynyl, cycloalkyl,
cycloalkenyl,
substituted or unsubstituted phenyl,
a 5- or 6-membered heterocyclic radical having one or two heteroatoms selected from the group consisting of oxygen, sulfur and nitrogen,
cycloalkanimino, phthalimido, succinimido, or a radical $-CH_2-CH(OH)-CH_2(OH)$, etc., $R^3$ and $R^4$ have the meanings defined herein, or their agriculturally acceptable salts possess herbicidal activity.

6 Claims, No Drawings

ISOXAZOLE(ISOTHIAZOLE)-5-CARBOXAMIDES

The present invention relates to substituted isoxazole- and isothiazole-5-carboxamides and their use for controlling undesirable plant growth.

Isoxazole- and isothiazolecarboxylic acids and their derivatives are known. These are 5-aminocarbonyl-3-methylisoxazole-4-carboxylic acid, ethyl 5-aminocarbonyl-3-methylisoxazole-4-carboxylate, isothiazole-4,5-dicarboxamide and 5-carbamoylisothiazole-4-carboxylic acid (J. Chem. Soc. Perkin Trans. I 1982, 2391; J. Heterocycl. Chem. 22 (1985), 1561 and J. Chem. Soc. 1959, 3061). Possible uses of these substances are not described.

We have found that isoxazole(isothiazole)-5-carboxamides of the formula Ia

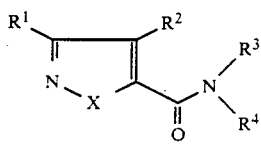

where
X is oxygen or sulfur,
$R^1$ is hydrogen,
$C_1-C_{10}$-alkyl which is unsubstituted or substituted by $C_1-C_3$-alkoxy, $C_1-C_3$-haloalkoxy, halogen, cyano or phenyl which may be substituted by halogen, $C_1-C_4$-alkyl, $C_1-C_4$-haloalkyl, $C_1-C_4$-alkoxy, $C_1-C_4$-haloalkoxy, $C_1-C_4$-alklthio, $C_1-C_4$-haloalkylthio, cyano or nitro, $C_1-C_4$-alkoxy,
$C_3-C_8$-cycloalkyl which is unsubstituted or substituted by $C_1-C_4$-alkyl or halogen,
a 5-membered or 6-membered heterocyclic radical having one or two heteroatoms selected from the group consisting of oxygen, sulfur and nitrogen, which may be substituted by $C_1-C_4$-alkyl, carboxyl or $C_1-C_4$-alkoxycarbonyl,
or phenyl which is unsubstituted or substituted by $C_1-C_6$-alkyl, $C_1-C_6$-haloalkyl, $C_1-C_6$-alkoxy, $C_1-C_6$-haloalkoxy, $C_1-C_8$-alkylthio, $C_1-C_6$-haloalkylthio, halogen, nitro or cyano,
$R^2$ is formyl, 4,5-dihydrooxazol-2-yl or a radical of the formula $COYR^5$ or $CONR^6R^7$, where
Y is oxygen or sulfur,
$R^5$ is hydrogen,
$C_1-C_8$-alkyl which may be substituted by $C_1-C_4$-alkoxy, $C_1-C_4$-alkoxy-$C_1-C_4$-alkoxy, halogen, cyano, hydroxyl, trimethylsilyl, $C_1-C_4$-alkylthio, $C_1-C_4$-alkylamino, $C_1-C_4$-dialkylamino, $C_1-C_4$-alkylsulfinyl, $C_1-C_4$-alkylsulfonyl, carboxyl, $C_1-C_4$-alkoxycarbonyl, $C_1-C_4$-dialkylaminocarbonyl, $C_1-C_4$-dialkoxyphosphonyl, alkyliminooxy, benzyloxy, benzoyl which is unsubstituted or substituted by $C_1-C_4$-alkyl, $C_1-C_3$-alkoxy or halogen, or phenyl which is unsubstituted by $C_1-C_4$-alkyl, $C_1-C_4$-alkoxy, $C_1-C_4$-haloalkyl, halogen, nitro or cyano, or may be substituted by thienyl, furyl, tetrahydrofuryl, phthalimido or pyridyl,
$C_3-C_8$-alkenyl which is unsubstituted or substituted by phenyl which may be substituted by $C_1-C_4$-alkyl, $C_1-C_4$-alkoxy, $C_1-C_4$-haloalkyl, halogen, nitro or cyano, $C_3-C_5$-haloalkenyl,
$C_3-C_8$-alkynyl which is unsubstituted or substituted by hydroxyl or $C_1-C_4$-alkoxy,
$C_3-C_6$-cycloalkyl,
$C_5$- or $C_6$-cycloalkenyl,
phenyl which is unsubstituted or substituted by $C_1-C_4$-alkyl, $C_1-C_4$-alkoxy, $C_1-C_4$-haloalkyl, halogen, nitro, cyano, $C_1-C_4$-alkoxycarbonyl or acylamino,
a 5-membered or 6-membered heterocyclic radical having one or two heteroatoms selected from the group consisting of oxygen, sulfur and nitrogen or a benzotriazole radical,
$C_6$- or $C_7$-cycloalkylimino, phthalimido, succinimido, or a radical

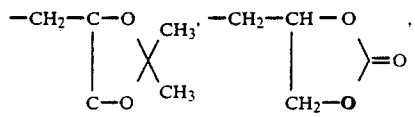

$-CH_2-CH(OH)-CH_2(OH)$ or one equivalent of a cation from the group consisting of the alkali metals, alkaline earth metals, manganese, copper, iron, ammonium and substituted ammonium, or a radical

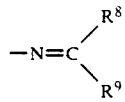

where $R^8$ and $R^9$ independently of one another are each $C_1-C_4$-alkyl, $C_2-C_5$-alkoxyalkyl, $C_3-C_8$-cycloalkyl, phenyl or furyl or together form a methylene chain of the formula $-(CH_2)_m-$, where m is from 4 to 7, and $R^9$ is additionally hydrogen,
$R^6$ is hydrogen, $C_1-C_8$-alkyl or $C_3-C_8$-cycloalkyl and
$R^7$ is hydrogen or $C_1-C_8$-alkyl, or
$R^6$ and $R^7$ form a methylene chain having 4 or 5 members,
$R^3$ is hydrogen,
$C_1-C_8$-alkyl which is unsubstituted or substituted by hydroxyl, halogen, $C_1-C_4$-alkoxy, $C_1-C_4$-alkylthio or $C_1-C_4$-dialkylamino
or $C_3-C_8$-cycloalkyl which is unsubstituted or substituted by $C_1-C_4$-alkyl, halogen or $C_1-C_4$-haloalkyl, and
$R^4$ is hydrogen, hydroxyl, $C_1-C_4$-alkoxy,
$C_1-C_{10}$-alkyl which is unsubstituted or substituted by $C_1-C_4$-alkoxy, $C_1-C_4$-haloalkoxy, $C_1-C_4$-alkylthio, $C_1-C_4$-dialkylamino, halogen, $C_3-C_6$-cycloalkyl or phenyl which may be substituted by halogen, cyano, nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-halo-alkylthio,
$C_3-C_{10}$-alkynyl or
$C_3-C_{10}$-alkenyl which is unsubstituted or substituted by halogen or $C_1-C_4$-alkoxy,
$C_3-C_8$-cycloalkyl which is unsubstituted or substituted by
$C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, halogen, nitro or cyano,
$C_1-C_4$-dialkylamino, a 3-membered to 6-membered heterocyclic radical which is unsubstituted or substituted by $C_1-C_6$-alkyl, $C_1-C_6$-haloalkyl or halogen and has one or two heteroatoms selected from the group consisting of oxygen, sulfur and unsubstituted or methylsubstituted nitrogen, naphthyl, or phenyl which is unsubstituted or substituted by $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitrogen, cyano, formyl, $C_1$–$C_6$-alkanoyl or $C_1$–$C_6$-haloalkanoyl, or $R^3$ and $R^4$ together form a radical of the structure $-(CH_2)_n-Y_p-(CH_2)_q-$, where n and q are each 1, 2 or 3, p is 0 or 1 and Y is oxygen, sulfur or N-methyl, or the radical of the formula $$-(CH_2)_2-CO-$$

and their agriculturally acceptable salts possess herbicidal activity.

The methyl, alkoxy, alkenyl and alkynyl radicals $R^1$, $R^3$, $R^4$, $R^5$, $R^6$ and $R^7$ may be straight-chain or branched and are preferably of 1 to 4 carbon atoms. The same applies to the alkyl radicals which may be present as substituents in the radicals $R^1$, $R^3$, $R^4$, $R^5$, $R^6$ and $R^7$, and to the alkyl groups in the haloalkyl, alkoxy, haloalkoxy, alkylthio, haloalkylthio, dialkylamino, alkanoyl, haloalkanoyl and alkoxycarbonyl radicals.

Preferred halogen substituents are chlorine substituents.

The heterocyclic radicals $R^1$ are saturated or unsaturated. Suitable examples are tetrahydropyranyl, tetrahydrofuryl, pyrazolyl, thienyl, furyl, pyridyl and tetrahydrofuryl. These radicals may be substituted by $C_1$–$C_4$-alkyl, carboxyl or $C_1$–$C_4$-alkylcarbonyl.

The heterocyclic radicals $R^5$ may be saturated or unsaturated. Suitable radicals are thienyl, furyl, tetrahydrofuryl, triazolyl, imidazolyl, tetrahydropyranyl, pyridyl, morpholino and piperidino.

Saturated or unsaturated heterocyclic radicals $R^4$ are, for example, tetrahydropyranyl, tetrahydrofuryl, thiazolyl, pyridyl, morpholino, piperidino and pyrimidyl.

The novel compounds I can form addition salts, for example with inorganic and organic acids or with alkyl halides, or, if one of the substituents has acidic properties, they can be reacted with inorganic and organic bases to give salts. The present invention also relates to such salts, to the extent that they are agriculturally acceptable.

Isoxazole(isothiazole)-5-carboxamides which are preferred herbicidal active ingredients are those of the formula Ia, where $R^3$ is hydrogen.

Other compounds of the formula Ia which are preferred active ingredients are those in which X is oxygen or sulfur, $R^1$ is hydrogen or $C_1$–$C_4$-alkyl, $R^2$ is $COYR^5$, $R^3$ is hydrogen and $R^4$ is $C_1$–$C_4$-alkyl or $C_3$–$C_8$-cycloalkyl. In these compounds, $R^5$ is preferably hydrogen, $C_1$–$C_4$-alkyl, or phenyl which is unsubstituted or substituted by $C_1$–$C_4$-alkyl, $C_1$–$C_4$-haloalkyl, $C_1$–$C_4$-alkoxy, $C_1$–$C_4$-alkylthio or halogen, or a radical

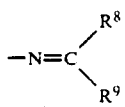

where $R^8$ and $R^9$ in turn are preferably each $C_1$–$C_4$-alkyl.

Isoxazole(isothiazole)-5-carboxamides of the formula

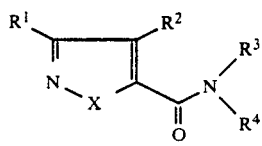

where X, $R^1$, $R^2$, $R^3$ and $R^4$ have the meanings stated for formula Ia, with the proviso that X is sulfur when $R^1$ is $CH_3$, $R^2$ is COOH or $COOC_2H_5$ and $R^3$ and $R^4$ are each hydrogen, and that X is oxygen when $R^1$ is hydrogen, $R^2$ is COOH or $CONH_2$ and $R^3$ and $R^4$ are each hydrogen, are novel.

The isoxazole(isothiazole)-5-carboxamides of the formula I or Ia can be prepared by the following methods:

1. A process for the preparation of compounds of the formula Ib and Ia, where $R^2$ is $COOR^5$ and $R^3$ is hydrogen or $C_1$–$C_8$-alkyl (cf. Scheme 1), is based on the reaction of a dialkyl isoxazole- or isothiazole-4,5-dicarboxylate II ($R^8=C_1$–$C_8$-alkyl) with an aqueous base and subsequent reaction with a mineral acid to give a carboxylic acid III. Particularly suitable dicarboxylates II are lower alkyl esters ($R^5=R^8=C_1$–$C_4$-alkyl), dimethyl and diethyl esters being particularly preferred.

The reaction is carried out by treating a dialkyl dicarboxylate II with a strong base for example NaOH, KOH or Ca(OH)$_2$, at from about 0° to 80° C., preferably from 0° to 50° C., in an organic solvent, e.g. methanol or ethanol. In general, about one equivalent of the strong base is used in aqueous solution. When the reaction is complete, the mixture is cooled and acidified with a strong mineral acid, for example hydrochloric acid or sulfuric acid. The resulting carboxylic acid III can be isolated in a conventional manner, for example by filtration under suction or by extraction with an organic solvent.

To convert the carboxylic acid III into the carbonyl halide IV, the acid III is reacted in a conventional manner with an inorganic acid halide, such as thionyl chloride, a phosphorus trihalide or a phosphorus pentahalide, the chlorides being preferred. Advantageously, the inorganic acid halide is used in an amount of from 1 to 5, preferably from 1 to 2, molar equivalents. The reaction can be carried out in the absence of a solvent or in the presence of an inert organic solvent, for example benzene or toluene, at from room temperature to the boiling point of the inorganic acid halide or of the inert organic solvent. In some cases, the addition of a catalyst, such as dimethylformamide or 4-dimethylaminopyridine, may be advantageous. When the reaction is complete, the acyl halide IV can be isolated in a conventional manner, for example by distilling off the excess inorganic acid halide and the organic solvent and then distilling the acyl chloride IV under atmospheric or reduced pressure.

The carboxamides Ib are obtained from the carbonyl halides by reaction with an amine V. For this purpose, it is advantageous if the carbonyl halide, in an inert organic solvent, such as dichloroethane, or an ether, such as diethyl ether or methyl tert-butyl ether, is reacted with an amine V, likewise dissolved in an organic solvent. The amine V is advantageously used in from 2 to 5, preferably from 2 to 3, times the molar amount in order to bind the resulting hydrogen halide. The reaction may also be carried out in the presence of an auxiliary base, such as a tertiary amine, e.g. triethylamine. In this case, from 1 to 1.5 molar equivalents of amine V are sufficient. The reaction temperature may be from 0° to 50° C., preferably from 0° to 20° C. The reaction is generally complete after from 1 to 12 hours. The mixture can be worked up in a conventional manner, for example by hydrolysis with water and extraction of the product of the formula Ib with an organic solvent and evaporation of the organic solvent. The product of the formula Ib can be purified, for example, by recrystallization or chromatography.

The 4-alkoxycarbonylisoxazole-5-carboxamides or 4-alkoxycarbonylisothiazole-5-carboxamides Ib can be converted into the free carboxylic acids Ic by reaction with an aqueous base followed by reaction with a mineral acid. The reaction is carried out by treating the esters Ib, in an organic solvent, e.g. methanol or ethanol, with a base, e.g. NaOH, KOH or Ca(OH)$_2$, at from 0° to 80° C., preferably from 0° to 50° C. In general, about 1-3, preferably 1-1.5, equivalents of the strong base are used in aqueous solution. When the reaction is complete, the mixture is acidified with a strong mineral acid, for example hydro-chloric acid or sulfuric acid, while cooling. The resulting carboxylic acids Ic can be isolated by filtration under suction or by extraction with an organic solvent and evaporation of this organic solvent. The acids Ic may be further purified by recrystallizing or chromatographing them.

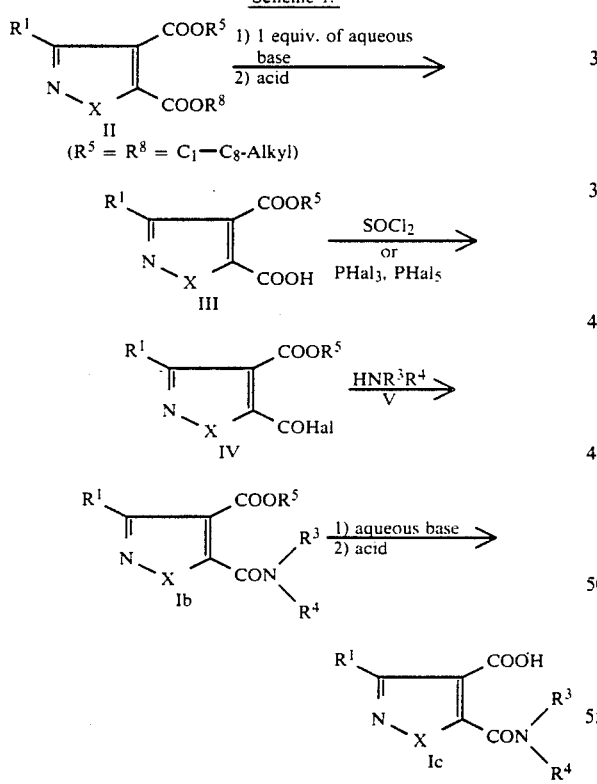

The dialkyl isoxazole- and isothiazole-4,5-dicarboxylates II required as starting materials for this process are known from the literature (J. Org. Chem. 43 (1978), 3736; Chem. Pharm. Bull. 28 (1980), 3296; Tetrahedron 30 (1974), 1365); those which are unknown can be prepared by methods generally known from the literature.

2. A further process for the preparation of the compounds Id is based on the reaction of an isoxazole- or isothiazole-5-carbonyl halide VI with an amine V. Preferred carbonyl halides VI are the chlorides. In this procedure, it is advantageous to react the carbonyl halide, in an inert organic solvent, such as dichloromethane, or an ether, such as diethyl ether or methyl tert-butyl ether, with an amine V, likewise dissolved in an organic solvent. The amine V is advantageously used in from 2 to 5, preferably from 2 to 3, times the molar amount in order to bind the resulting hydrogen halide. The reaction may also be carried out in the presence of an auxiliary base, for example a tertiary amine (triethylamine). In this case, from 1 to 1.5 molar equivalents of amine V are sufficient. The reaction temperature may be from 0° to 50° C., preferably from 0° to 20° C. The reaction is generally complete after from 1 to 12 hours. The mixture can be worked up in a conventional manner, for example by hydrolysis with water and extraction of the product VII with an organic solvent and evaporation of the organic solvent.

The isoxazole- or isothiazolecarboxamides VII are converted into the 5-aminocarbonylisoxazole-4-carboxylic acids or 5-aminocarbonylisothiazole-4-carboxylic acids of the formula Id by reaction with an alkyllithium, preferably with the addition of a solvent which is inert under the reaction conditions, such as diethyl ether or tetrahydrofuran. As a rule, the reaction is carried out under a nitrogen atmosphere at from −70° C. −80° C. In this process, the alkyllithium compound is generally used in from 2 to 3 times the molar amount, based on amide of the formula VII used. When the reaction is complete, the mixture is treated with carbon dioxide, preferably in an inert solvent, such as diethyl ether or, for example, tetrahydrofuran, the desired products of the formula Id, where $R^2$ is carboxyl, being obtained.

Using the same process, it is also possible to obtain isoxazole- and isothiazolecarboxamides of the formula Id, where $R^2$ is formyl, if dimethylformamide is used instead of the carbon dioxide. Working up in a conventional manner gives substituted 4-formylisoxazole-5-carboxamides or 4-formylisothiazole-5-carboxamides of the formula Id.

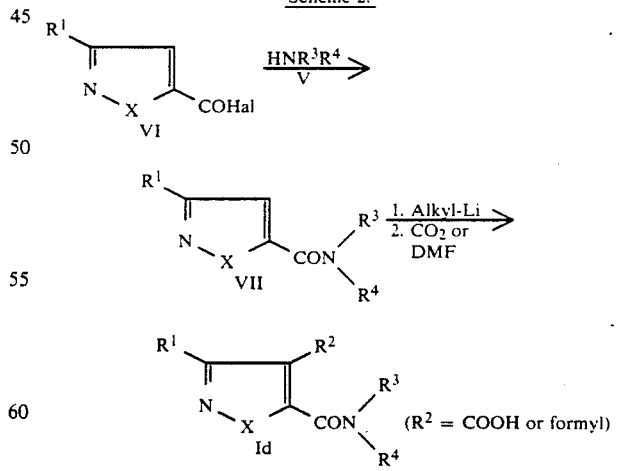

The isoxazole- and isothiazole-5-carbonyl halides VI required as starting materials for this process are known from the literature. Those which are unknown can be prepared from the corresponding carboxylic acids VIII in a conventional manner, as described above.

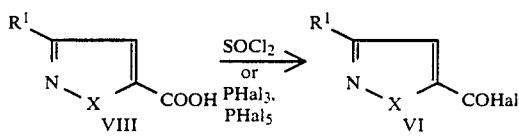

The carboxylic acids VIII required for this purpose are likewise known from the literature (Chem. Ber. 106 (1973), 3345, J. Chem. Soc. 1959, 3061, J. Chem. Soc. 1963, 2032, Adv. in Heterocyclic Chem. 14 (1972), 1); those which are unknown can be prepared by methods generally known from the literature, for example from the corresponding alcohols or aldehydes by oxidation or from the corresponding nitriles by hydrolysis.

3. Another process leads to compounds Ie, in which $R^2$ is $COOR^5$ and $R^5$ is $C_1$–$C_8$-alkyl which is unsubstituted or substituted by $C_1$–$C_4$-alkoxy, $C_1$–$C_4$-alkoxy-$C_1$–$C_4$-alkoxy, halogen, $C_1$–$C_4$-alkylthio, $C_1$–$C_4$-alkylsulfinyl, $C_1$–$C_4$-alkylsulfonyl, $C_1$–$C_4$-alkoxycarbonyl or benzyloxy or by phenyl which may be substituted by $C_1$–$C_4$-alkyl, $C_1$–$C_4$-alkoxy, $C_1$–$C_4$-haloalkyl, halogen, nitro or cyano, or $R^5$ is $C_3$–$C_6$-cycloalkyl or is $C_3$–$C_8$-alkenyl which is unsubstituted or substituted by phenyl which may be substituted by $C_1$–$C_4$-alkyl, $C_1$–$C_4$-alkoxy, $C_1$–$C_4$-haloalkyl, halogen, nitro or cyano, or $R^5$ is $C_3$–$C_8$-alkynyl, $C_6$- or $C_7$-cycloalkylimino, succinimido or a radical of the formula

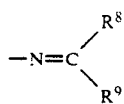

by reaction of an acid Ic with a corresponding alcohol IX in the presence of a strong mineral acid, for example hydrochloric acid or sulfuric acid, at from 0° to 100° C. preferably from 20° to 50° C. As a rule, an excess of the alcohol IX is used, but it is also possible to employ an inert solvent.

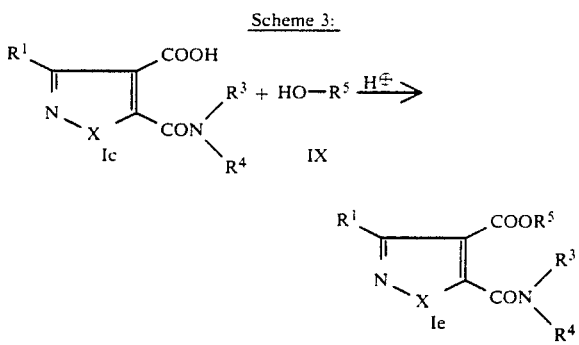

4. In a further process for the preparation of the compounds of the formula Ie, an acid Ic is reacted with an alcohol or thiol IX in the presence of a dehydrating agent (e.g. dicyclohexylcarbodiimide (DCC)) at from −20° to 50° C., preferably from 0° to 30° C. As a rule, the starting materials are used for the reaction in a roughly stoichiometric amount. The reaction is preferably carried out in the presence of an inert solvent, for example tetrahydrofuran, dichloromethane or toluene.

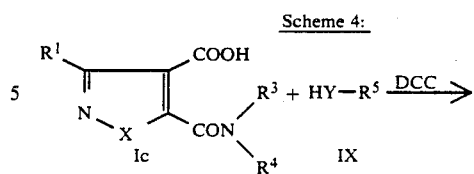

(where Y is O or S).

5. Another process for the preparation of the compounds Ic is based on the reaction of an alkyl carboxylate If with an alkali metal alkoxide X, such as sodium alkoxide or potassium alkoxide, with a corresponding alcohol IX in a conventional manner at from 20° C. to the boiling point of the selected alcohol IX.

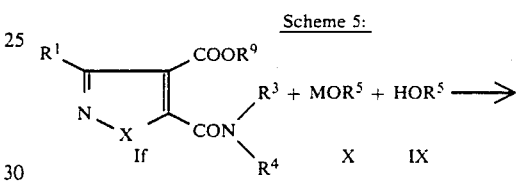

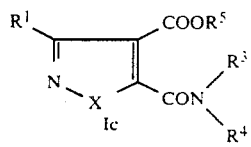

($R^9$ = methyl or ethyl)

6. Compounds of the formula Ig, where $R^2$ is $COOR^2$ and $R^5$ is a salt-forming cation, for example an alkali metal, alkaline earth metal, ammonium or substituted ammonium ion, are obtained by reacting a substituted isoxazole- or isothiazole-4-carboxylic acid Ic with one equivalent of the salt-forming cation. If the cation in question is an inorganic cation, for example sodium, potassium or calcium, the acid Ic is advantageously dissolved or suspended in water or in a lower alcohol or a mixture of these, and one equivalent of the salt-forming cation is added. The salt-forming cation may be used, for example, in the form of its hydroxide, carbonate or bicarbonate, preferably in the form of its hydroxide. The reaction is generally complete after a few minutes, and the mixture can be worked up in a conventional manner, for example by precipitation and filtration under suction or by evaporation of the solvent. To prepare compounds Ig in which $B^\oplus$ is ammonium or organic ammonium, the acid Ic is dissolved or suspended in an organic solvent, e.g. diethyl ether, tetrahydrofuran or dioxane, and the mixture is treated with one equivalent of ammonia, an amine or a tetraalkylammonium hydroxide.

Among the amines which may be used, the following should be mentioned: methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamines, n-propanolamine, isopropanolamine, diethanolamine, N,N-diethylethanolamine, N-ethylpropanolamine, N-butylethanolamine, allylamine, n-buten-2-ylamine, n-penten-2-ylamine, 2,3-dimethylbuten-2-ylamine, dibuten-2-ylamine, n-hexen-2-ylamine, propylenediamine, tallowamine, cyclopentylamine, cyclohexylamine, dicyclohexylamine, piperidine, morpholine and pyrrolidine.

In the case of tetraalkylammonium hydroxides, for example, tetramethyl-, tetraethyl- or trimethylbenzylammonium hydroxide may be used. As a rule, the ammonium salt or organic ammonium salt is precipitated from the solution and can be isolated by a conventional method. Alternatively, the salt of the formula Ig can also be obtained by evaporating the solvent.

Scheme 6:

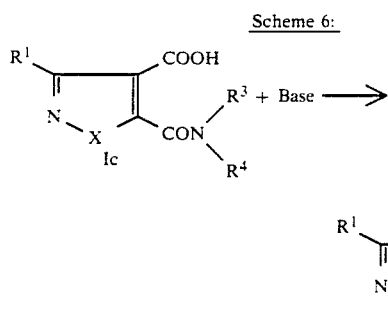

7. Another process leads to compounds Ih in which $R^2$ is $CONR^6R^7$. It consists in reacting an ester Ib with a primary or secondary amine XI. The process is carried out by reacting an ester Ib with from 1 to 50 times the molar amount of amine XI, in the presence or absence of an organic solvent, at from room temperature to the boiling point of the amine or of the organic solvent. Preferred esters Ib are lower alkyl esters, particularly the methyl and ethyl esters. The reaction products Ih can be isolated in a conventional manner, for example by filtration under suction or evaporation of the solution and, if required, can be further purified by recrystallization or chromatography.

Scheme 7:

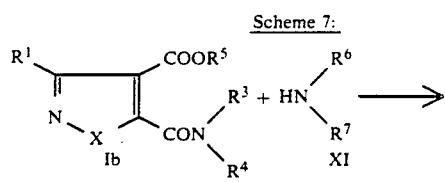

Scheme 7:

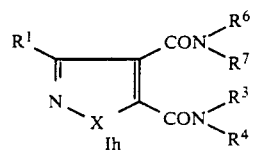

8. In another process for the synthesis of the compounds Ib, a dialkyl isoxazole- or isothiazole-4,5-dicarboxylate II is reacted with an amine V.

Particularly suitable dialkyl esters II are lower alkyl esters, preferably dimethyl esters or diethyl esters. The reaction is carried out by treating a dialkyl dicraboxylate II with about one equivalent of a primary or secondary amine V at from 0° to 100° C., preferably from 50° to 80° C., in an organic solvent, for example an alcohol, such as methanol or ethanol. When the reaction is complete, the mixture is cooled and filtered under suction or evaporated down. The resulting product of the formula Ib can be further purified by a conventional standard method, such as recrystallization or chromatography.

Scheme 8:

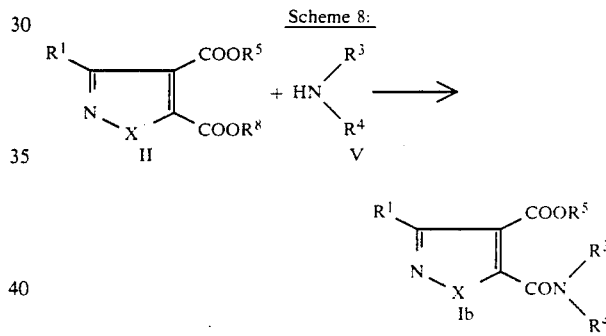

9. Compounds of the formula Ii can be obtained by reacting a substituted isothiazole-4,5-dicarboxylic anhydride XII with an amine V. The reaction is advantageously carried out by initially taking the anhydride XII in an inert solvent, such as an ether or a halohydrocarbon, and adding dropwise about a molar amount of an amine V, if necessary likewise dissolved in an inert solvent. After the reaction is complete, the reaction product is filtered off under suction or isolated by evaporating the solvent used. In some case, the isomeric amides XIII may be formed in this process, the amide Ii generally being the preferred ones.

Scheme 9:

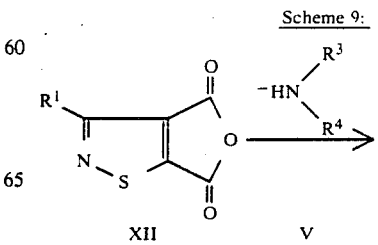

-continued
Scheme 9:

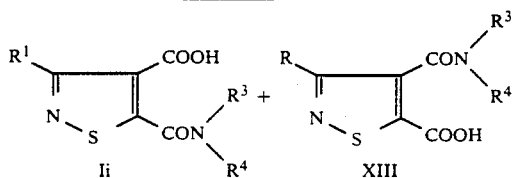

The isothiazole-4,5-dicarboxylic anhydrides XII required as starting materials for this process are known form the literature (J. Chem. Soc. 1959, 3061); those which are unknown can be synthesised by methods which are generally known from the literature.

10. In another process for the preparation of compounds of the formula Ik, an acid Ic is reacted with an alcohol or thiol XIV in the presence of a 1-methyl-2-halopyridinium iodide at from 20° to 80° C., preferably from 30° to 40° C. The reaction is carried out in the presence of an inert solvent, e.g. dichloromethane or toluene. The process is known in principle from the literature (Chem. Lett. 1045 (1975); ibid. 13 (1976); ibid. 49 (1976)).

Scheme 10:

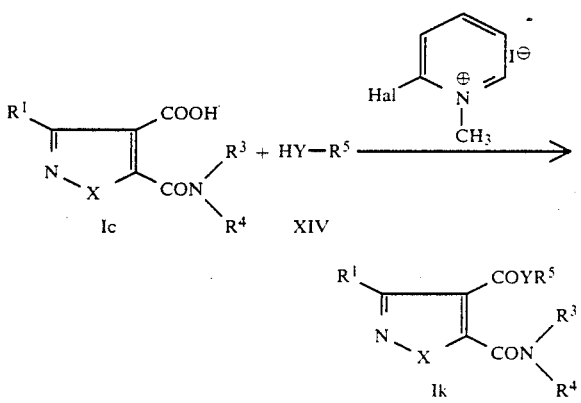

The Examples which follow illustrate the preparation of the intermediates for the synthesis of the compounds I or Ia.

EXAMPLE a 11.7 g of aniline are added dropwise to 10.0 g of 3-ethylisoxazole-5-carbonyl chloride in 150 ml of dichloromethane, while cooling with ice. The mixture is stirred overnight at room temperature, water and concentrated hydrochloric acid are added and the organic phase is separated off, washed with sodium bicarbonate solution and evaporated down to give 11.8 g of 3-ethylisoxazole-5-carboxanilide as colorless crystals of melting point 122°–124° C.

For example, the isoxazole-5-carboxamides VII can be synthesized in a similar manner:

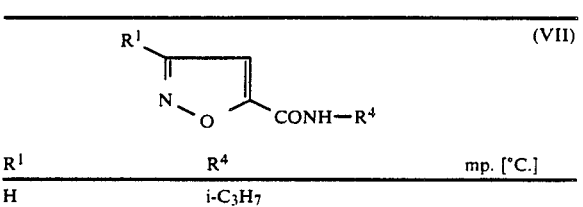

| $R^1$ | $R^4$ | mp. [°C.] |
|---|---|---|
| H | i-$C_3H_7$ | |
| H | tert -$C_4H_9$ | 103–106 |
| H | cyclo-$C_3H_5$ | |
| H | cyclo-$C_6H_{11}$ | |
| H | $C_6H_5$ | |
| $CH_3$ | H | 167–171 |
| $CH_3$ | i-$C_3H_7$ | 92–93 |
| $CH_3$ | tert -$C_4H_9$ | 55–60 |
| $CH_3$ | 1-Ethylcyclohexyl | oil |
| $CH_3$ | 4-Methyltetrahydro-pyran-4-yl | 63–65 |
| $CH_3$ | $C_6H_5$ | 145–147 |
| $CH_3$ | 4-Cl—$C_6H_4$ | 216–219 |
| $CH_3$ | 3-$CF_3$—$C_6H_4$ | 146–148 |
| $C_2H_5$ | i-$C_3H_7$ | 85–87 |
| $C_2H_5$ | tert -$C_4H_9$ | 67–70 |
| $C_2H_5$ | 4-Cl—$C_6H_4$ | 170–173 |
| $C_2H_5$ | 3-$CF_3$—$C_6H_4$ | 121–122 |
| i-$C_3H_7$ | H | |
| i-$C_3H_7$ | $CH_3$ | 69–73 |
| i-$C_3H_7$ | $C_2H_5$ | 69–72 |
| i-$C_3H_7$ | n-$C_3H_7$ | 79–80 |
| i-$C_3H_7$ | i-$C_3H_7$ | 122–125 |
| i-$C_3H_7$ | n-$C_4H_9$ | 67–68 |
| i-$C_3H_7$ | sec -$C_4H_9$ | 133–135 |
| i-$C_3H_7$ | i-$C_4H_9$ | 85–86 |
| i-$C_3H_7$ | tert -$C_4H_9$ | 116–118 |
| i-$C_3H_7$ | —$C(CH_3)_2C_2H_5$ | 118–120 |
| i-$C_3H_7$ | —$C(CH_3)_2C_3H_7$ | 33–34 |
| i-$C_3H_7$ | —$C(CH_3)_2CH_2C(CH_3)_3$ | 65–66 |
| i-$C_3H_7$ | —$C(CH_3)_2CH_2SCH_3$ | 42 |
| i-$C_3H_7$ | —$CH_2CH_2SCH_3$ | |
| i-$C_3H_7$ | —$CH_2CH_2CH_2SCH_3$ | 34–36 |
| i-$C_3H_7$ | —$CH_2CH_2OCH_3$ | oil |
| i-$C_3H_7$ | —$CH_2CH_2N(CH_3)_2$ | oil |
| i-$C_3H_7$ | cyclo-$C_3H_5$ | 88–90 |
| i-$C_3H_7$ | cyclo-$C_6H_{11}$ | 152–154 |
| i-$C_3H_7$ | 1-Methylcyclohexyl | |
| i-$C_3H_7$ | 1-Ethylcyclohexyl | 50–51 |
| i-$C_3H_7$ | 4-Methyltetrahydro-pyran-4-yl | 94–96 |
| i-$C_3H_7$ | 4-Ethyltetrahydro-pyran-4-yl | 50–51 |
| i-$C_3H_7$ | —$C(CH_3)_2$-cyclo$C_6H_{11}$ | 83 |
| i-$C_3H_7$ | —$CH_2CH=CH_2$ | 65–66 |
| i-$C_3H_7$ | —$C(CH_3)_2CH=CH_2$ | 99–106 |
| i-$C_3H_7$ | —$C(CH_3)_2C\equiv CH$ | 85–86 |
| i-$C_3H_7$ | —$CH_2$—$C_6H_5$ | 79–81 |
| i-$C_3H_7$ | —$C(CH_3)_2C_6H_5$ | |
| i-$C_3H_7$ | —$CH_2$—$C(CH_3)_3$ | 87–89 |
| i-$C_3H_7$ | —$C_6H_5$ | 106–108 |
| i-$C_3H_7$ | 4-Cl—$C_6H_4$ | 176–178 |
| i-$C_3H_7$ | 3-$CF_3$—$C_6H_4$ | 74–75 |
| tert.-$C_4H_9$ | i-$C_3H_7$ | 120–122 |
| tert.-$C_4H_9$ | tert-$C_4H_9$ | 129–132 |
| tert.-$C_4H_9$ | $C_6H_5$ | 121–122 |
| tert.-$C_4H_9$ | 4-Cl—$C_6H_4$ | 158–161 |
| tert.-$C_4H_9$ | 3-$CF_3$—$C_6H_4$ | 104–108 |
| cyclo-$C_6H_{11}$ | i-$C_3H_7$ | 139–140 |
| cyclo-$C_6H_{11}$ | tert -$C_4H_9$ | 121–122 |
| cyclo-$C_6H_{11}$ | $C_6H_5$ | 144–146 |
| cyclo-$C_6H_{11}$ | 4-Cl—$C_6H_4$ | |
| cyclo-$C_6H_{11}$ | cyclo-$C_6H_{11}$ | |
| cyclo-$C_6H_{11}$ | $C_6H_5$ | 180–181 |
| Tetrahydropyran-3-yl | i-$C_3H_7$ | 102–104 |
| Tetrahydropyran-3-yl | tert -$C_4H_9$ | 110–114 |
| Tetrahydropyran-3-yl | cyclo-$C_3H_5$ | 108–110 |
| Tetrahydropyran-3-yl | cyclo-$C_6H_{11}$ | |
| Tetrahydropyran-3-yl | $C_6H_5$ | 149–151 |
| $C_6H_5$ | i-$C_3H_7$ | |
| $C_6H_5$ | tert -$C_4H_9$ | |
| $C_6H_5$ | cyclo-$C_3H_5$ | |
| $C_6H_5$ | cyclo-$C_6H_{11}$ | |
| $C_6H_5$ | $C_6H_5$ | |
| 4-Cl—$C_6H_4$ | i-$C_3H_7$ | 166–171 |
| 4-Cl—$C_6H_4$ | tert -$C_4H_9$ | 128–132 |
| 4-Cl—$C_6H_4$ | $C_6H_5$ | 229–232 |
| 4-Cl—$C_6H_4$ | 4-Cl—$C_6H_4$ | |
| 4-Cl—$C_6H_4$ | 3-$CF_3$—$C_6H_4$ | 163–165 |
| cyclo-$C_3H_5$ | i-$C_3H_7$ | 114–117 |
| cyclo-$C_3H_5$ | tert -$C_4H_9$ | 106–107 |
| cyclo-$C_3H_5$ | $C_6H_5$ | 180–186 |
| | | mp. [°C.]/ $^1$H.NMR |

-continued

| R¹ | R⁴ | (CDCl₃) [ppm] |
|---|---|---|
| i-C₃H₇ | cyclo-C₅H₉ | 119-121 |
| i-C₃H₇ | Tetrahydrofur-3-yl | 75-78 |
| i-C₃H₇ | Thiazol-2-yl | 165-168 |
| i-C₃H₇ | 5-Methylthiazol2-yl | 149-153 |
| i-C₃H₇ | 5-Ethylthiazol2-yl | 157-163 |
| i-C₃H₇ | 5-n-Propylthiazol-yl | 140-145 |
| i-C₃H₇ | CH(CH₃)CH₂CN | 88-92 |
| i-C₃H₇ | —C(CH₃)₂—CH₂CN | 95-97 |
| i-C₃H₇ | OC₂H₅ | 33-35 |
| i-C₃H₇ | Pyrid-2-yl | 104-106 |
| i-C₃H₇ | Pyrid-3-yl | 150-152 |
| i-C₃H₇ | Pyrid-4-yl | 185-187 |
| i-C₃H₇ | Pyrimid-2-yl | 94-99 |
| n-C₃H₇ | i-C₃H₇ | 108-110 |
| n-C₃H₇ | cyclo-C₃H₅ | 104-106 |
| n-C₃H₇ | tert-C₄H₉ | 85-86 |
| n-C₃H₇ | C₆H₅ | 118-119 |
| n-C₃H₇ | cyclo-C₆H₁₁ | 136-137 |
| s-C₄H₉ | i-C₃H₇ | 150-152 |
| s-C₄H₉ | cyclo-C₃H₅ | 107-111 |
| s-C₄H₉ | tert-C₄H₉ | 138-142 |
| s-C₄H₉ | C₆H₅ | 99-101 |
| i-C₃H₇ | N(CH₃)₂ | 131-133 |
| CH₃ | N(CH₃)₂ | 111-113 |
| CH₃ | Morpholino | 190-192 |
| CH₃ | Piperidino | 158-161 |
| CH₃ | CH₃ | 146-148 |
| i-C₃H₇ | Piperidino | 133-135 |
| i-C₃H₇ | Morpholino | 178-179 |
| CH₃ | C₂H₅ | 97-99 |
| neo-C₅H₁₁ | CH₃ | 128-130 |
| neo-C₅H₁₁ | i-C₃H₇ | 85-88 |
| neo-C₅H₁₁ | cyclo-C₃H₅ | 109-112 |
| neo-C₅H₁₁ | tert-C₄H₉ | 97-99 |
| neo-C₅H₁₁ | C₆H₅ | 137-140 |
| n-C₄H₉ | CH₃ | 74-76 |
| n-C₄H₉ | i-C₃H₇ | 97-100 |
| n-C₄H₉ | cyclo-C₃H₅ | 82-86 |
| n-C₄H₉ | tert-C₄H₉ | 60-64 |
| n-C₄H₉ | C₆H₅ | 113-120 |
| cyclo-C₅H₉ | tert-C₄H₉ | 114-115 |
| cyclo-C₅H₉ | CH₃ | 88-89 |
| cyclo-C₅H₉ | cyclo-C₃H₅ | 108-109 |
| cyclo-C₅H₉ | C₆H₅ | 146-148 |
| n-C₄H₉ | OCH₃ | 62-66 |
| CH₃—O—CH₂ | tert-C₄H₉ | 50-55 |
| CH₃—O—CH₂ | cyclo-C₃H₅ | 55-60 |
| 2-Methoxyphenyl | tert-C₄H₉ | 119-120 |
| 2-Methoxyphenyl | cyclo-C₃H₅ | 160-163 |
| i-C₃H₇ | CH₂-cyclo-C₃H₅ | 77-80 |
| n-C₄H₉ | —CH₂-cyclo-C₃H₅ | 102-105 |
| CH₃O—CH(CH₃)— | tert-C₄H₉ | 76-79 |
| cyclo-C₃H₅ | cyclo-C₅H₉ | 148-149 |
| 2,6-Difluorophenyl | tert-C₄H₉ | 118-122 |
| 2,6-Difluorophenyl | cyclo-C₃H₅ | 128-132 |
| CH₃ | cyclo-C₄H₇ | 114-115 |
| i-C₃H₇ | cyclo-C₄H₇ | 84-85 |
| CH₃O | tert-C₄H₉ | 65-68 |

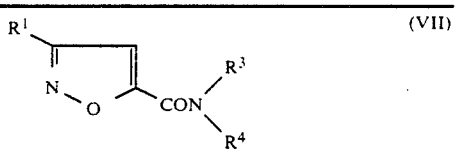

(VII)

| R¹ | R³ | R⁴ | pm. [°C.] |
|---|---|---|---|
| i-C₃H₇ | CH₃ | CH₃ | |
| i-C₃H₇ | C₂H₅ | C₂H₅ | oil |

EXAMPLE b 65 g of diethyl 3-methylisoxazole-4,5-dicarboxylate, dissolved in 100 ml of ethanol, are added dropwise to 18.9 g of potassium hydroxide in 100 ml of water at room temperature. After 16 hours, the mixture is poured onto 300 ml of water and extracted with ether, and the aqueous phase is acidified with concentration hydrochloric acid. Extracting with dichloromethane and evaporating down give 3-methyl-4-ethoxycarbonylisoxazole-5-carboxylic acid as colorless crystals of melting point 54°-58° C.

EXAMPLE c

A solution of 14.9 g of NaOH in 120 ml of water and 150 ml of methanol is added dropwise to 85.5 g of dimethyl 3-ethylisothiazole-4,5-dicarboxylate in 300 ml of methanol, while cooling with ice. After 2 hours, the mixture is evaporated down, 1.5 l of water are added to the residue and the mixture is stirred, and extracted with ether. The aqueous phase is acidified with concentrated hydrochloric acid and extracted by shaking with dichloromethane. The organic phases are evaporated down to give 76.4 g of 3-ethyl-4-methoxycarbonylisothiazole-5-carboxylic acid of melting point 43°-45° C.

For example, the isoxazole(isothiazole)-5-carboxylic acids III can be synthesized similarly to Examples b and c.

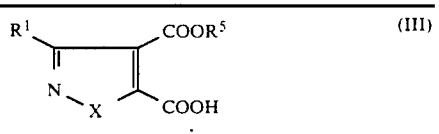

(III)

| R¹ | R⁵ | X | mp. [°C.] |
|---|---|---|---|
| H | CH₃ | O | |
| H | C₂H₅ | O | |
| H | CH₃ | S | |
| H | C₂H₅ | S | |
| CH₃ | CH₃ | O | |
| CH₃ | CH₃ | S | 75-81 |
| CH₃ | C₂H₅ | S | |
| C₂H₅ | CH₃ | O | |
| C₂H₅ | C₂H₅ | O | |
| C₂H₅ | C₂H₅ | S | |
| n-C₃H₇ | CH₃ | O | |
| n-C₃H₇ | C₂H₅ | O | |
| n-C₃H₇ | CH₃ | S | |
| n-C₃H₇ | C₂H₅ | S | |
| i-C₃H₇ | CH₃ | O | |
| i-C₃H₇ | C₂H₅ | O | |
| i-C₃H₇ | CH₃ | S | oil |
| i-C₃H₇ | C₂H₅ | S | |
| s-C₄H₉ | CH₃ | O | |
| s-C₄H₉ | C₂H₅ | O | |
| s-C₄H₉ | CH₃ | S | |
| s-C₄H₉ | C₂H₅ | S | |
| tert-C₄H₉ | CH₃ | O | |
| tert-C₄H₉ | C₂H₅ | O | |
| tert-C₄H₉ | CH₃ | S | |
| tert-C₄H₉ | C₂H₅ | S | |
| cyclo-C₃H₅ | CH₃ | O | |
| cyclo-C₃H₅ | C₂H₅ | O | |
| cyclo-C₃H₅ | CH₃ | S | |
| cyclo-C₃H₅ | C₂H₅ | S | |
| cyclo-C₆H₁₁ | CH₃ | O | |
| cyclo-C₆H₁₁ | C₂H₅ | O | |
| cyclo-C₆H₁₁ | CH₃ | S | |
| cyclo-C₆H₁₁ | C₂H₅ | S | |
| Tetrahydropyran-3-yl | CH₃ | O | |
| Tetrahydropyran-3-yl | C₂H₅ | O | |
| Tetrahydropyran-3-yl | CH₃ | S | |
| Tetrahydropyran-3-yl | C₂H₅ | S | |
| C₆H₅ | CH₃ | O | |
| C₆H₅ | C₂H₅ | O | |
| C₆H₅ | CH₃ | S | 139-141 |
| C₆H₅ | C₂H₅ | S | |

PREPARATION EXAMPLES FOR COMPOUNDS I AND Ia

EXAMPLE 1

2.9 g of isopropylamine are added dropwise to 10 g of diethyl 3-methylisoxazole-4,5-dicarboxylate, dissolved in 100 ml of methanol, and the mixture is then refluxed. After 7 hours, the mixture is evaporated down and the remaining oil is chromatographed over silica gel (using 9:1 toluene/acetone). Methyl 5-isopropylaminocarbonyl-3-methylisoxazole-4-carboxylate is obtained as colorless crystals of melting point 64°-66° C. (compound No. 1005).

EXAMPLE 2

2.6 g of the ester from Example 1 and 0.8 g of potassium hydroxide in 20 ml of water and 20 ml of ethanol are stirred for 16 hours at room temperature. Thereafter, the mixture is diluted with water, acidified with concentrated hydrochloric acid and extracted by shaking with dichloromethane. Evaporating down gives 1.8 g of 5-isopropylaminocarbonyl-3-methylisoxazole-4-carboxylic acid as colorless crystals of melting point 86°-92° C. (compound No. 1004).

EXAMPLE 3

70 ml of n-butyllithium (1.6 molar solution in n-hexane) are added dropwise, at −70° C., to 9.0 g of the anilide from Example a, dissolved in 200 ml of absolute tetrahydrofuran. Stirring is carried out for half an hour and the reaction mixture is poured onto 500 g of solid carbon dioxide. After standing overnight, the mixture is evaporated down and the residue is partitioned between H$_2$O, sodium hydroxide solution and ethyl acetate. By evaporating down the ethyl acetate phase, 2.0 g of starting material can be recovered. Acidification of the aqueous phase with concentrated hydrochloric acid and filtration under suction give 8.30 g of 5-anilinocarbonyl-3-ethylisoxazole-4-carboxylic acid as colorless crystals of melting point 150°-152° C. (compound No. 1015).

EXAMPLE 4

5.0 g of 5-tert-butylaminocarbonyl-3-methylisoxazole-4-carboxylic acid are dissolved in 200 ml of methanol, and 5 ml of concentrated H$_2$SO$_4$ are added. After 2 days, the mixture is evaporated down, the residue is partitioned between ethyl acetate and water and the organic phase is evaporated down. 4.0 g of methyl 5-tert-butylaminocarbonyl-3-methylisoxazole-4-carboxylate are obtained as a colorless oil (compound No. 1007).

H-NMR (CDCl$_3$): d=1.48 (s; 9H), 2.50 (s; 3H), 3.99 (s; 1H), 9.42 (bs; 1H, NH).

EXAMPLE 5 a) 3-Ethyl-4-methoxycarbonylisothiazole-5-carbonyl chloride 73 g of the carboxylic acid from Example c and 80 g of thionyl chloride in 200 ml of toluene are refluxed in the presence of a little dimethylformamide until the evolution of gas is complete. The crude carbonyl chloride which remains in quantitative yield after evaporation is directly reacted further.

b) Methyl 5-isopropylaminocarbonyl-3-ethylisothiazole-4-carboxylate 8.4 g of isopropylamine are slowly added dropwise to 16.5 g of the crude acyl chloride from a) in 200 ml of dichloromethane, while cooling with ice. Stirring is carried out overnight, hydrolysis is effected with 150 ml of water and the organic phase is separated off, washed with bicarbonate solution, dilute hydrochloric acid and water and then evaporated down. 16.2 g of methyl 5-isopropylaminocarbonyl-3-ethylthiazole-4-carboxylate of melting point 55°-56° C. (compound No. 3007) are obtained.

EXAMPLE 6

2.8 g of KOH in 30 ml of water are added to 11 g of the ester from Example 5 in 50 ml of ethanol, and the mixture is stirred overnight at room temperature. It is diluted with 150 ml of water and extracted with ether, and the aqueous phase is acidified with concentrated hydrochloric acid. Extraction by shaking with dichloromethane and evaporation give 10 g of 5-isopropylaminocarbonyl-3-ethylisothiazole-4-carboxylic acid of melting point 138°-140° C. (compound 3006).

EXAMPLE 7

4.0 g of methyl 5-tert-butylaminocarbonyl-3-methylisoxazole-4-carboxylate and 50 ml of concentrated ammonia are refluxed for 3 hours. After cooling, the mixture is diluted with water and extracted with dichloromethane and the organic phase is evaporated down. 5-tert-butylaminocarbonyl-3-methylisoxazole-4-carboxamide is obtained as colorless crystals of melting point 155°-158° C. (compound No. 1).

EXAMPLE 8

56 ml of butyllithium (1.6 molar solution in n-hexane) are added dropwise, at −78° C., to 8 g of the tert-butylamine of 3-methylisoxazole-5-carboxylic acid in 150 ml of tetrahydrofuran. The mixture is stirred for 1 hour, after which 22 ml of dimethylformamide are slowly added dropwise. The mixture is allowed to reach room temperature overnight and is hydrolyzed with water, neutralized with concentrated hydrochloric acid and extracted with ether. The oil which remains after evaporation is chromatographed over silica gel using cyclohexane/ethyl acetate. The tert-butylamide of 4-formyl-3-methylisoxazole-5-carboxylic acid is obtained as the first fraction, in the form of pale yellow crystals of melting point 36°-38° C. (compound No. 2).

EXAMPLE 9 a) 3-Methyl-4-ethoxycarbonylisoxazole-5-carbonylchloride 13.3 g of the carboxylic acid from Example b and 20 ml of thionyl chloride are refluxed in the presence of a little dimethylformamide until the evolution of gas is complete. The crude carbonyl chloride which remains in quantitative yield after evaporation is directly reacted further.

b) 3.4 g of diethylamine are slowly added dropwise to 5 g of the crude acyl chloride from a) in 100 g of dichloromethane, while cooling with ice. Stirring is carried out overnight, hydrolysis is effected with water and the organic phase is separated off, washed with bicarbonate and then evaporated down. 5.0 g of ethyl 5-diethylaminocarbonyl-3-methylisoxazole-4-carboxylate are obtained as a brown oil (compound No. 3).

H-NMR (CDCl₃): δ=1.15 (t; 3H), 1.27 and 1.31 (2t; 6H), 2.50 (s; 3H), 3.17 (q; 2H), 3.58 (q; 2H), 4.28 (q; 2H).

EXAMPLE 10

5.0 g of the ester from Example 9 and 1.4 g of potassium hydroxide in 10 ml of water and 20 ml of ethanol are stirred at room temperature. When the reaction is complete, the mixture is diluted with water and extracted with dichloromethane. Thereafter, the aqueous phase is acidified with hydrochloric acid and extracted with dichloromethane, and the organic phase is evaporated down. 3.0 g of 5-diethylaminocarbonyl-3-methylisoxazole-4-carboxylic acid are obtained as a pale oil (compound No. 4).

H-NMR (CDCl₃): δ=1.28 and 1.32 (2t; 6H), 2.60 (s; 3H), 3.59 and 3.62 (2q; 4H), 10.50 (bs; 1H, COOH).

EXAMPLE 11

A mixture of 1.2 g of 2-methylpropane-2-thiol, 3.0 g of 5-tert-butylaminocarbonyl-3-methylisoxazole-4-carboxylic acid and 5.9 g of tri-n-butylamine in 20 ml of dichloromethane is added dropwise to a stirred suspension of 4.1 g of 1-methyl-2-chloropyridinium iodide in 40 ml of dichloromethane at room temperature. The mixture is refluxed for 3 hours, the solvent is stripped off under reduced pressure and the crude product is purified by column chromatography over silica gel. 2.1 g of the tert-butyl thioester of 5-tert-butylaminocarbonyl-3-methylisoxazole-4-carboxylic acid are obtained as a yellow oil (compound No. 2003).

For example, the compounds mentioned in Tables 1 to 3 below can be prepared similarly to Examples 1 to 10.

TABLE 1

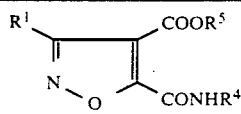

| No. | R¹ | R⁵ | R⁴ | mp [°C.]/¹H-NMR (CDCl₃) [ppm] |
|---|---|---|---|---|
| 1001 | H | H | i-C₃H₇ | |
| 1002 | H | H | tert.-C₄H₉ | oil 1.55(s; 9H), 7.50 (bs; 1H, NH), 8.78(s; 1H) |
| 1003 | CH₃ | H | H | 266–268 |
| 1004 | CH₃ | H | i-C₃H₇ | 86–92 |
| 1005 | CH₃ | CH₃ | i-C₃H₇ | 64–66 |
| 1006 | CH₃ | H | tert.-C₄H₉ | 92–94 |
| 1007 | CH₃ | CH₃ | tert.-C₄H₉ | |
| 1008 | CH₃ | H | 1-ethylcyclohexyl | 119–121 |
| 1009 | CH₃ | H | 4-methyltetrahydropyran-4-yl | 80–87 |
| 1010 | CH₃ | H | C₆H₅ | 204–210 |
| 1011 | CH₃ | H | 4-Cl—C₆H₄ | 233–237 |
| 1012 | CH₃ | H | 3-CF₃—C₆H₄ | 188–191 |
| 1013 | C₂H₅ | H | i-C₃H₇ | 63–66 |
| 1014 | C₂H₅ | H | tert.-C₄H₉ | 53–58 |
| 1015 | C₂H₅ | H | C₆H₅ | 150–152 |
| 1016 | C₂H₅ | H | 4-Cl—C₆H₄ | 193–196 |
| 1017 | C₂H₅ | H | 3-CF₃—C₆H₄ | 160–162 |
| 1018 | i-C₃H₇ | H | H | |
| 1019 | i-C₃H₇ | H | CH₃ | 147–148 |
| 1020 | i-C₃H₇ | H | C₂H₅ | 100–101 |
| 1021 | i-C₃H₇ | H | n-C₃H₇ | 85–86 |
| 1022 | i-C₃H₇ | H | i-C₃H₇ | 98–99 |
| 1023 | i-C₃H₇ | H | n-C₄H₉ | 96–97 |
| 1024 | i-C₃H₇ | H | i-C₄H₉ | 112–114 |
| 1025 | i-C₃H₇ | H | sec-C₄H₉ | oil 1.00(t; 3H), 1.32(d; 3H), 1.37(d; 6H), 1.64(quint; 2H), 3.78(sept; 1H), 4.15 (m; 1H), 7.00 (bs; 1H,NH) |
| 1026 | i-C₃H₇ | H | tert.-C₄H₉ | 94–98 |
| 1027 | i-C₃H₇ | H | C(CH₃)₂C₂H₅ | 44–46 |
| 1028 | i-C₃H₇ | H | C(CH₃)₂C₃H₇ | 52–53 |
| 1029 | i-C₃H₇ | H | C(CH₃)₂CH₂C(CH₃)₃ | 89–91 |
| 1030 | i-C₃H₇ | H | C(CH₃)₂CH₂SCH₃ | oil 1.35(d; 3H), 1.56(s; 6H), 2.18(s; 3H), 2.99(s; 2H), 3.77(sept; 1H), 7.30(bs; 1H, NH) |
| 1031 | i-C₃H₇ | H | CH₂CH₂SCH₃ | |
| 1032 | i-C₃H₇ | H | CH₂CH₂CH₂SCH₃ | 116–118 |
| 1033 | i-C₃H₇ | H | CH₂CH₂OCH₃ | 69–71 |
| 1034 | i-C₃H₇ | H | CH₂CH₂N(CH₃)₂ | |
| 1035 | i-C₃H₇ | H | cyclo-C₃H₅ | 74–76 |

TABLE 1-continued $$\begin{array}{c} R^1 \\ \parallel \\ N_{\diagdown O} \end{array} \begin{array}{c} COOR^5 \\ \diagup \\ \diagdown CONHR^4 \end{array}$$

| No. | R¹ | R⁵ | R⁴ | mp [°C.]/¹H-NMR (CDCl₃) [ppm] |
|---|---|---|---|---|
| 1036 | i-C₃H₇ | H | cyclo-C₆H₁₁ | 112–114 |
| 1037 | i-C₃H₇ | H | 1-ethylcyclohexyl | 89–90 |
| 1038 | i-C₃H₇ | H | 4-methyltetrahydro-pyran-4-yl | 129–130 |
| 1039 | i-C₃H₇ | H | 1-C(CH₃)₂-cycloC₆H₁₁ | 144–146 |
| 1040 | i-C₃H₇ | H | CH₂CH=CH₂ | 92–94 |
| 1041 | i-C₃H₇ | H | C(CH₃)₂CH=CH₂ | oil; 1.35(d; 6H), 1.62(s; 6H), 3.78(sept; 1H), 5.20(d; 1H), 5.25(d; 1H), 6.10(dd; 1H), 7.10(bs; 1H, NH) |
| 1042 | i-C₃H₇ | H | CH₂C₆H₅ | oil 1.30(d; 6H), 3.74(sept; 1H), 4.70(d; 2H), 7.35(bs; 5H), 7.85(bt; 1H, NH) |
| 1043 | i-C₃H₇ | H | C(CH₃)₂C₆H₅ | |
| 1044 | i-C₃H₇ | H | CH₂C(CH₃)₃ | 76 |
| 1045 | i-C₃H₇ | H | C₆H₅ | 138–140 |
| 1046 | i-C₃H₇ | H | 4-Cl—C₆H₄ | 170–173 |
| 1047 | i-C₃H₇ | H | 3-CF₃—C₆H₄ | 127 |
| 1048 | tert.-C₄H₉ | H | i-C₃H₇ | 84–85 |
| 1049 | tert.-C₄H₉ | H | tert.-C₄H₉ | 129–133 |
| 1050 | tert.-C₄H₉ | H | C₆H₅ | 132–137 |
| 1051 | tert.-C₄H₉ | H | 4-Cl—C₆H₄ | 188–191 |
| 1052 | tert.-C₄H₉ | H | 3-CF₃—C₆H₄ | 160–162 |
| 1053 | cyclo-C₆H₁₁ | H | i-C₃H₇ | 116–118 |
| 1054 | cyclo-C₆H₁₁ | H | tert.-C₄H₉ | 158–159 |
| 1055 | cyclo-C₆H₁₁ | H | cyclo-C₃H₅ | 142–143 |
| 1056 | cyclo-C₆H₁₁ | H | cyclo-C₆H₁₁ | |
| 1057 | cyclo-C₆H₁₁ | H | C₆H₅ | 198–199 |
| 1058 | 4-Cl—C₆H₄ | H | i-C₃H₇ | 165–168 |
| 1059 | 4-Cl—C₆H₄ | H | tert.-C₄H₉ | 165–168 |
| 1060 | 4-Cl—C₆H₄ | H | C₆H₅ | 220 |
| 1061 | 4-Cl—C₆H₄ | H | 4-Cl—C₆H₄ | |
| 1062 | 4-Cl—C₆H₄ | H | 3-CF₃—C₆H₄ | 209–211 |
| 1063 | i-C₃H₇ | succinimido | cyclo-C₃H₅ | 108–109 |
| 1064 | CH₃ | H | C(CH₃)₂C≡CH | 80–87 |
| 1065 | CH₃ | C₂H₅ | C(CH₃)₂C≡CH | 82–86 |
| 1066 | CH₃ | Na⊕ | tert.-C₄H₉ | 220 |
| 1067 | CH₃ | K⊕ | tert.-C₄H₉ | 288 |
| 1068 | CH₃ | H₃N⊕CH(CH₃)₂ | tert.-C₄H₉ | 184–187 |
| 1069 | CH₃ | H₃N⊕—CH₂CH₂OH | tert.-C₄H₉ | 124–126 |
| 1070 | C₂H₅ | Na⊕ | tert.-C₄H₉ | 150 |
| 1071 | C₂H₅ | K⊕ | tert.-C₄H₉ | 220 |
| 1072 | C₂H₅ | H₃N⊕—CH(CH₃)₂ | tert.-C₄H₉ | 170–172 |
| 1073 | C₂H₅ | H₃N⊕—CH₂CH₂OH | tert.-C₄H₉ | 105–108 |
| 1074 | C₂H₅ | succinimido | tert.-C₄H₉ | 163–165 |
| 1075 | C₂H₅ | —N=C(CH₃)₂ | tert.-C₄H₉ | 68–70 |
| 1076 | C₂H₅ | CH₂C≡CH | tert.-C₄H₉ | oil 1.35(t; 3H), 1.48(s; 9H), 2.63(t; 1H), 2.96; 4.98 (d; 2H), 8.95(bs; 1H, NH) |
| 1077 | C₂H₅ | CH₂CH₂OC₂H₅ | tert.-C₄H₉ | 74–76 |
| 1078 | cyclo-C₃H₅ | H | i-C₃H₇ | 78–80 |
| 1079 | cyclo-C₃H₅ | H | tert.-C₄H₉ | 87–88 |
| 1080 | cyclo-C₃H₅ | H | C₆H₅ | 162–163 |
| 1081 | cyclo-C₆H₁₁ | succinimido | i-C₃H₇ | 126–127 |
| 1082 | cyclo-C₆H₁₁ | succinimido | tert.-C₄H₉ | 172–174 |
| 1083 | cyclo-C₆H₁₁ | succinimido | C₆H₅ | 176–177 |
| 1084 | tetrahydro-pyran-3-yl | H | i-C₃H₇ | 157–160 |
| 1085 | tetrahydro-pyran-3-yl | H | tert.-C₄H₉ | 91–95 |
| 1086 | tetrahydro-pyran-3-yl | H | cyclo-C₃H₅ | 158–160 |
| 1087 | tetrahydro-pyran-3-yl | H | C₆H₅ | 152–157 |
| 1088 | CH₃ | pyrid-3-yl-methyl | tert.-C₄H₉ | |
| 1089 | CH₃ | thien-2-yl-methyl | tert.-C₄H₉ | |
| 1090 | CH₃ | —CH₂—CH₂—N(CH₃)₂ | tert.-C₄H₉ | |

TABLE 1-continued $$\begin{array}{c}R^1 \diagdown \diagup COOR^5 \\ \| \\ N \diagdown O \diagdown CONHR^4\end{array}$$

| No. | $R^1$ | $R^5$ | $R^4$ | mp [°C.]/$^1$H-NMR (CDCl$_3$) [ppm] |
|---|---|---|---|---|
| 1091 | CH$_3$ | —CH$_2$—CH$_2$N$^\oplus$(CH$_3$)$_3$I$^\oplus$ | tert.-C$_4$H$_9$ | |
| 1092 | CH$_3$ | —CH$_2$—CF$_3$ | tert.-C$_4$H$_9$ | |
| 1093 | CH$_3$ | —CH$_2$—C(CH$_3$)=CH$_2$ | tert.-C$_4$H$_9$ | |
| 1094 | CH$_3$ | —CH$_2$C(Cl)=CH$_2$ | tert.-C$_4$H$_9$ | |
| 1095 | CH$_3$ | —CH$_2$—C≡C—CH$_2$OH | tert.-C$_4$H$_9$ | |
| 1096 | CH$_3$ | —CH$_2$—CH—O\<br>            \|         \>C(CH$_3$)$_2$\<br>      CH$_2$—O | tert.-C$_4$H$_9$ | |
| 1097 | CH$_3$ | —CH$_2$—CH—OH\<br>          \|\<br>       CH$_2$OH | tert.-C$_4$H$_9$ | |
| 1098 | CH$_3$ | —CH$_2$—CH—O\<br>          \|   \>=O\<br>     CH$_2$—O | tert.-C$_4$H$_9$ | |
| 1099 | CH$_3$ | phenethyl | tert.-C$_4$H$_9$ | |
| 1100 | CH$_3$ | —CH(C$_6$H$_5$)COOCH$_3$ | tert.-C$_4$H$_9$ | |
| 1101 | CH$_3$ | cyclo-C$_6$H$_{11}$ | tert.-C$_4$H$_9$ | |
| 1102 | CH$_3$ | —CH$_2$—OCH$_2$—C$_6$H$_5$ | tert.-C$_4$H$_9$ | |
| 1103 | CH$_3$ | tetrahydro-pyran-2-yl | tert.-C$_4$H$_9$ | |
| 1104 | CH$_3$ | tetrahydro-fur-2-yl | tert.-C$_4$H$_9$ | |
| 1105 | CH$_3$ | (4-bromobenzoyl)-methyl | tert.-C$_4$H$_9$ | |
| 1106 | CH$_3$ | (4-methoxybenzoyl)methyl | tert.-C$_4$H$_9$ | |
| 1107 | CH$_3$ | —CH(COOCH$_3$)$_2$ | tert.-C$_4$H$_9$ | |
| 1108 | CH$_3$ | phthalimidomethyl | tert.-C$_4$H$_9$ | |
| 1109 | CH$_3$ | —CH$_2$—CH$_2$—Si(CH$_3$)$_3$ | tert.-C$_4$H$_9$ | |
| 1110 | CH$_3$ | —CH$_2$—CH$_2$—O—N=C(CH$_3$)$_2$ | tert.-C$_4$H$_9$ | |
| 1111 | CH$_3$ | —CH$_2$—PO(OC$_2$H$_5$)$_2$ | tert.-C$_4$H$_9$ | |
| 1112 | CH$_3$ | fur-2-yl-methyl | tert.-C$_4$H$_9$ | |
| 1113 | CH$_3$ | tetrahydrofur-2-yl-methyl | tert.-C$_4$H$_9$ | |
| 1114 | CH$_3$ | pyrid-2-ylmethyl | tert.-C$_4$H$_9$ | |
| 1115 | CH$_3$ | pyrid-4-ylmethyl | tert.-C$_4$H$_9$ | |
| 1116 | CH$_3$ | piperidino | tert.-C$_4$H$_9$ | |
| 1117 | CH$_3$ | phthalimido | tert.-C$_4$H$_9$ | |
| 1118 | CH$_3$ | benzotriazol-1-yl | tert.-C$_4$H$_9$ | |
| 1119 | CH$_3$ | —N=CH—C$_6$H$_5$ | tert.-C$_4$H$_9$ | |
| 1120 | CH$_3$ | —N=CH—(fur-2-yl) | tert.-C$_4$H$_9$ | |
| 1121 | CH$_3$ | —CH(CH$_3$)CH(OCH$_3$)$_2$ | tert.-C$_4$H$_9$ | |
| 1122 | CH$_3$ | —CH$_2$—CON(C$_2$H$_5$)$_2$ | tert.-C$_4$H$_9$ | |
| 1123 | CH$_3$ | N(C$_2$H$_5$)$_2$ | tert.-C$_4$H$_9$ | |
| 1124 | C$_2$H$_5$ | cyclo-C$_6$H$_{11}$ | tert.-C$_4$H$_9$ | |
| 1125 | C$_2$H$_5$ | —CH$_2$—OCH$_2$—C$_6$H$_5$ | tert.-C$_4$H$_9$ | |
| 1126 | C$_2$H$_5$ | tetrahydro-pyran-2-yl | tert.-C$_4$H$_9$ | |
| 1127 | C$_2$H$_5$ | tetrahydro-fur-2-yl | tert.-C$_4$H$_9$ | |
| 1128 | C$_2$H$_5$ | (4-bromobenzoyl)-methyl | tert.-C$_4$H$_9$ | |
| 1129 | C$_2$H$_5$ | (4-methoxybenzoyl)-methyl | tert.-C$_4$H$_9$ | |
| 1130 | C$_2$H$_5$ | —CH(COOCH$_3$)$_2$ | tert.-C$_4$H$_9$ | |
| 1131 | C$_2$H$_5$ | phthalimidomethyl | tert.-C$_4$H$_9$ | |
| 1132 | C$_2$H$_5$ | —CH$_2$—CH$_2$—Si(CH$_3$)$_3$ | tert.-C$_4$H$_9$ | |
| 1133 | C$_2$H$_5$ | —CH$_2$—CH$_2$—O—N=C(CH$_3$)$_2$ | tert.-C$_4$H$_9$ | |
| 1134 | C$_2$H$_5$ | —CH$_2$—PO(OC$_2$H$_5$)$_2$ | tert.-C$_4$H$_9$ | |
| 1135 | C$_2$H$_5$ | fur-2-ylmethyl | tert.-C$_4$H$_9$ | |

TABLE 1-continued $$\text{structure with } R^1, COOR^5, N, O, CONHR^4$$

| No. | $R^1$ | $R^5$ | $R^4$ | mp [°C.]/$^1$H-NMR (CDCl$_3$) [ppm] |
|---|---|---|---|---|
| 1136 | $C_2H_5$ | tetrahydrofur-2-yl-methyl | tert.-$C_4H_9$ | |
| 1137 | $C_2H_5$ | pyrid-2-yl-methyl | tert.-$C_4H_9$ | |
| 1138 | $C_2H_5$ | pyrid-4-yl-methyl | tert.-$C_4H_9$ | |
| 1139 | $C_2H_5$ | pyrid-3-yl-methyl | tert.-$C_4H_9$ | |
| 1140 | $C_2H_5$ | thien-2-yl-methyl | tert.-$C_4H_9$ | |
| 1141 | $C_2H_5$ | —CH$_2$—CH$_2$—N(CH$_3$)$_2$ | tert.-$C_4H_9$ | |
| 1142 | $C_2H_5$ | —CH$_2$—CH$_2$N(CH$_3$)$_3^\oplus$ I$^\oplus$ | tert.-$C_4H_9$ | |
| 1143 | $C_2H_5$ | —CH$_2$—CF$_3$ | tert.-$C_4H_9$ | |
| 1144 | $C_2H_5$ | —CH$_2$—C(CH$_3$)=CH$_2$ | tert.-$C_4H_9$ | |
| 1145 | $C_2H_5$ | —CH$_2$C(Cl)=CH$_2$ | tert.-$C_4H_9$ | |
| 1146 | $C_2H_5$ | —CH$_2$—C≡C—CH$_2$OH | tert.-$C_4H_9$ | |
| 1147 | $C_2H_5$ | —CH$_2$—CH(CH$_2$—O—)(O—)C(CH$_3$)$_2$ (acetonide) | tert.-$C_4H_9$ | |
| 1148 | $C_2H_5$ | —CH$_2$—CH(OH)—CH$_2$OH | tert.-$C_4H_9$ | |
| 1149 | $C_2H_5$ | —CH$_2$—CH(CH$_2$—O—)(O—)C=O (carbonate) | tert.-$C_4H_9$ | |
| 1150 | $C_2H_5$ | phenethyl | tert.-$C_4H_9$ | |
| 1151 | $C_2H_5$ | —CH(C$_6$H$_5$)COOCH$_3$ | tert.-$C_4H_9$ | |
| 1152 | $C_2H_5$ | piperidino | tert.-$C_4H_9$ | |
| 1153 | $C_2H_5$ | phthalimido | tert.-$C_4H_9$ | |
| 1154 | $C_2H_5$ | benzotriazol-1-yl (—N bonded to benzotriazole) | tert.-$C_4H_9$ | |
| 1155 | $C_2H_5$ | —N=CH—C$_6$H$_5$ | tert.-$C_4H_9$ | |
| 1156 | $C_2H_5$ | —N=CH-(fur-2-yl) | tert.-$C_4H_9$ | |
| 1157 | $C_2H_5$ | —CH(CH$_3$)CH(OCH$_3$)$_2$ | tert.-$C_4H_9$ | |
| 1158 | $C_2H_5$ | —CH$_2$—CON(C$_2$H$_5$)$_2$ | tert.-$C_4H_9$ | |
| 1159 | $C_2H_5$ | N(C$_2$H$_5$)$_2$ | tert.-$C_4H_9$ | |
| 1160 | i-$C_3H_7$ | cyclo-$C_6H_{11}$ | tert.-$C_4H_9$ | |
| 1161 | i-$C_3H_7$ | —CH$_2$—OCH$_2$—C$_6$H$_5$ | tert.-$C_4H_9$ | |
| 1162 | i-$C_3H_7$ | tetrahydro-pyran-2-yl | tert.-$C_4H_9$ | |
| 1163 | i-$C_3H_7$ | tetrahydro-fur-2-yl | tert.-$C_4H_9$ | |
| 1164 | i-$C_3H_7$ | (4-bromobenzoyl)-methyl | tert.-$C_4H_9$ | |
| 1165 | i-$C_3H_7$ | (4-methoxybenzoyl)methyl | tert.-$C_4H_9$ | |
| 1166 | i-$C_3H_7$ | —CH(COOCH$_3$)$_2$ | tert.-$C_4H_9$ | |
| 1167 | i-$C_3H_7$ | phthalimidomethyl | tert.-$C_4H_9$ | |
| 1168 | i-$C_3H_7$ | —CH$_2$—Si(CH$_3$)$_3$ | tert.-$C_4H_9$ | 64–69 |
| 1169 | i-$C_3H_7$ | —CH$_2$—CH$_2$—O—N=C(CH$_3$)$_2$ | tert.-$C_4H_9$ | |
| 1170 | i-$C_3H_7$ | —CH$_2$—PO(OC$_2$H$_5$)$_2$ | tert.-$C_4H_9$ | |
| 1171 | i-$C_3H_7$ | fur-2-ylmethyl | tert.-$C_4H_9$ | |
| 1172 | i-$C_3H_7$ | tetrahydrofur-2-yl-methyl | tert.-$C_4H_9$ | |
| 1173 | i-$C_3H_7$ | pyrid-2-yl-methyl | tert.-$C_4H_9$ | oil; 1.30(s; 6H) 1.44 (s; 9H), 3.40 (sept; 1H) 5.52 (s; 2H) 7.20–8.64 (m; 4H), 8.60 (bs; 1H, NH) |

TABLE 1-continued

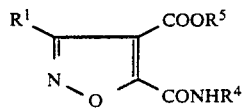

| No. | R[1] | R[5] | R[4] | mp [°C.]/$^1$H-NMR (CDCl$_3$) [ppm] |
|---|---|---|---|---|
| 1174 | i-C$_3$H$_7$ | pyrid-4-yl-methyl | tert.-C$_4$H$_9$ | |
| 1175 | i-C$_3$H$_7$ | pyrid-3-yl-methyl | tert.-C$_4$H$_9$ | |
| 1176 | i-C$_3$H$_7$ | thien-2-yl-methyl | tert.-C$_4$H$_9$ | |
| 1177 | i-C$_3$H$_7$ | —CH$_2$—CH$_2$—N(CH$_3$)$_2$ | tert.-C$_4$H$_9$ | |
| 1178 | i-C$_3$H$_7$ | —CH$_2$—CH$_2$N(CH$_3$)$_3^{\oplus}$I$^{\oplus}$ | tert.-C$_4$H$_9$ | |
| 1179 | i-C$_3$H$_7$ | —CH$_2$—CF$_3$ | tert.-C$_4$H$_9$ | |
| 1352 | i-C$_3$H$_7$ | —CH$_2$—C(CH$_3$)=CH$_2$ | tert.-C$_4$H$_9$ | |
| 1153 | i-C$_3$H$_7$ | —CH$_2$C(Cl)=CH$_2$ | tert.-C$_4$H$_9$ | |
| 1154 | i-C$_3$H$_7$ | —CH$_2$—C≡C—CH$_2$OH | tert.-C$_4$H$_9$ | |
| 1155 | i-C$_3$H$_7$ | —CH$_2$—CH(—O—C(CH$_3$)$_2$—O—CH$_2$—) (acetonide) | tert.-C$_4$H$_9$ | |
| 1156 | i-C$_3$H$_7$ | —CH$_2$—CH(OH)—CH$_2$OH | tert.-C$_4$H$_9$ | |
| 1157 | i-C$_3$H$_7$ | —CH$_2$—CH(—O—C(=O)—O—CH$_2$—) | tert.-C$_4$H$_9$ | |
| 1180 | i-C$_3$H$_7$ | phenethyl | tert.-C$_4$H$_9$ | |
| 1181 | i-C$_3$H$_7$ | —CH(C$_6$H$_5$)COOCH$_3$ | tert.-C$_4$H$_9$ | |
| 1182 | i-C$_3$H$_7$ | piperidino | tert.-C$_4$H$_9$ | |
| 1183 | i-C$_3$H$_7$ | phthalimido | tert.-C$_4$H$_9$ | |
| 1184 | i-C$_3$H$_7$ | benzotriazol-1-yl | tert.-C$_4$H$_9$ | |
| 1185 | i-C$_3$H$_7$ | —N=CH—C$_6$H$_5$ | tert.-C$_4$H$_9$ | |
| 1186 | i-C$_3$H$_7$ | —N=CH-(furan-2-yl) | tert.-C$_4$H$_9$ | |
| 1187 | i-C$_3$H$_7$ | —CH(CH$_3$CH)(OCH$_3$)$_2$ | tert.-C$_4$H$_9$ | |
| 1188 | i-C$_3$H$_7$ | —CH$_2$—CON(C$_2$H$_5$)$_2$ | tert.-C$_4$H$_9$ | 91–93 |
| 1189 | i-C$_3$H$_7$ | N(C$_2$H$_5$)$_2$ | tert.-C$_4$H$_9$ | |
| 1190 | CH$_3$ | —N=C(CH$_3$)$_2$ | tert.-C$_4$H$_9$ | 108–109 |
| 1191 | CH$_3$ | cyclohexanimino | tert.-C$_4$H$_9$ | 91–92 |
| 1192 | CH$_3$ | —N=C(cyclo-C$_3$H$_5$)$_2$ | tert.-C$_4$H$_9$ | 50–52 |
| 1193 | CH$_3$ | H | —N(CH$_3$)$_2$ | 225–227 |
| 1194 | CH$_3$ | H | piperidino | 162–164 |
| 1195 | CH$_3$ | CH$_2$—C≡CH | tert.-C$_4$H$_9$ | 90–95 |
| 1197 | CH$_3$ | 2-NO$_2$-4-F—C$_6$H$_3$ | tert.-C$_4$H$_9$ | oil; 1.44(s; 9H), 2.59(s; 3H), 7.24 and 8.30 (m; 3H), 8.16 (bs; 1H, NH) |
| 1198 | CH$_3$ | 3,5-(CF$_3$)$_2$—C$_6$H$_3$ | tert.-C$_4$H$_9$ | 156–159 |
| 1199 | CH$_3$ | H | CH$_3$ | 192–197 |
| 1200 | CH$_3$ | H | —OC$_2$H$_5$ | 145–148 |
| 1201 | CH$_3$ | H | cyclo-C$_4$H$_7$ | 141–142 |
| 1202 | CH$_3$ | H | cyclo-C$_3$H$_5$ | 135–137 |
| 1203 | CH$_3$ | —N=C(CH$_3$)$_2$ | cyclo-C$_3$H$_5$ | 91–93 |
| 1204 | CH$_3$ | H | C$_2$H$_5$ | 151–154 |
| 1205 | CH$_3$ | —N=C(CH$_3$)$_2$ | cyclo-C$_4$H$_7$ | 77–79 |
| 1207 | CH$_3$ | CH$_2$CO$_2$CH$_3$ | tert.-C$_4$H$_9$ | 88–89 |
| 1208 | C$_2$H$_5$ | succinimido | i-C$_3$H$_7$ | 132–136 |
| 1209 | n-C$_3$H$_7$ | H | cyclo-C$_6$H$_{11}$ | 132–134 |

TABLE 1-continued

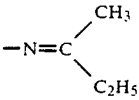

| No. | R¹ | R⁵ | R⁴ | mp [°C.]/¹H-NMR (CDCl₃) [ppm] |
|---|---|---|---|---|
| 1210 | n-C₃H₇ | H | tert.-C₄H₉ | 82–83 |
| 1211 | n-C₃H₇ | —N=C(CH₃)₂ | tert.-C₄H₉ | 66–68 |
| 1212 | n-C₃H₇ | succinimido | tert.-C₄H₉ | 126–129 |
| 1213 | n-C₃H₇ | succinimido | cyclo-C₃H₅ | 104–106 |
| 1214 | n-C₃H₇ | —N=C(CH₃)₂ | cyclo-C₃H₅ | oil 0.70(m; 2H), 0.90(m; 2H), 1.00(t; 3H), 1.78(m; 2H), 2.16 and 2.19 (2s; 6H), 2.92 (t; 2H), 3.00 (m; 1H), 9.24 (bs; 1H, NH) |
| 1215 | n-C₃H₇ | H | cyclo-C₃H₅ | 104–106 |
| 1216 | n-C₃H₇ | H | i-C₃H₇ | 70–71 |
| 1217 | n-C₃H₇ | —N=C(CH₃)₂ | i-C₃H₇ | 72–73 |
| 1218 | n-C₃H₇ | —N=C(CH₃)₂ | cyclo-C₆H₁₁ | 110–111 |
| 1219 | n-C₃H₇ | H | C₆H₅ | 165–166 |
| 1220 | i-C₃H₇ | —N=C(CH₃)₂ | tert.-C₄H₉ | 112–113 |
| 1221 | i-C₃H₇ | —N=C(CH₃)(C₂H₅) | tert.-C₄H₉ | 83–86 |
| 1222 | i-C₃H₇ | cyclohexanimino | tert.-C₄H₉ | 91–94 |
| 1223 | i-C₃H₇ | —N=C(cyclo-C₃H₅)₂ | tert.-C₄H₉ | 70–75 |
| 1224 | i-C₃H₇ | —N=C(CH₃)₂ | tetrahydrofur-3-yl | 104–106 |
| 1225 | i-C₃H₇ | succinimido | tetrahydrofur-3-yl | 160–162 |
| 1226 | i-C₃H₇ | H | tetrahydrofur-3-yl | oil 1.33(d; 6H), 2.40(m; 2H), 3.75(sept; 1H), 4.00(m; 4H), 4.75 (m; 1H), 8.25 (d; 1H,NH) |
| 1227 | i-C₃H₇ | H | OC₂H₅ | 134–135 |
| 1228 | i-C₃H₇ | succinimido | OC₂H₅ | 146–148 |
| 1229 | i-C₃H₇ | H | thiazol-2-yl | 195 |
| 1230 | i-C₃H₇ | H | 5-methyl-thiazol-2-yl | 248 |
| 1231 | i-C₃H₇ | H | 5-ethyl-thiazol-2-yl | 228–230 |
| 1232 | i-C₃H₇ | H | 5-n-propyl-thiazol-2-yl | 160–163 |
| 1233 | i-C₃H₇ | succinimido | tert.-C₄H₉ | 141–144 |
| 1234 | i-C₃H₇ | H | cyclo-C₄H₇ | 95–96 |
| 1235 | i-C₃H₇ | —N=C(CH₃)₂ | cyclo-C₄H₇ | 100–101 |
| 1236 | i-C₃H₇ | —N=C(CH₃)₂ | —N(CH₃)₂ | 129–131 |
| 1237 | i-C₃H₇ | H | —N(CH₃)₂ | 163–165 |
| 1238 | i-C₃H₇ | H | piperidino | 167–168 |
| 1239 | i-C₃H₇ | H | morpholino | 177–179 |
| 1240 | i-C₃H₇ | H | cyclo-C₅H₉ | 62–65 |
| 1241 | i-C₃H₇ | H | cyclopropylmethyl | 88–90 |
| 1242 | i-C₃H₇ | H | s-C₄H₉ | oil; 1.00(t; 3H), 1.34(d; 3H), 1.37(d; 6H), 1.66(quint; 2H), 3.78 (sept; 1H), 4.17(m; 1H), 7.04 (d, 1H, NH) |
| 1243 | i-C₃H₇ | —N=C(CH₃)₂ | s-C₄H₉ | oil; 0.98(t; 3H), 1.26(d, 3H), 1, 39 (d, 6H) 1.64 (quint; 2H), 2.16 and 2.18 (2s; 6H) 3.44 (sept; 1H), 4.10 (m, 1H), 8.54 (d, 1H, NH) |
| 1244 | i-C₃H₇ | H | mixture of 4-methyl-5-carboxy-thiazol-2-yl and 4-methyl-thiazol-2-yl | 197 |

TABLE 1-continued $$\begin{array}{c} R^1 \quad COOR^5 \\ \diagdown \!\!\! / \\ \| \\ N \quad CONHR^4 \\ \diagdown O \end{array}$$

| No. | R$^1$ | R$^5$ | R$^4$ | mp [°C.]/$^1$H-NMR (CDCl$_3$) [ppm] |
|---|---|---|---|---|
| 1245 | i-C$_3$H$_7$ | CH$_2$—CH=CH—C$_6$H$_5$ | tert.-C$_4$H$_9$ | 59–63 |
| 1246 | i-C$_3$H$_7$ | 4-CO$_2$CH$_3$C$_6$H$_4$ | tert.-C$_4$H$_9$ | 143–145 |
| 1247 | i-C$_3$H$_7$ | CH$_2$—CH$_2$—CN | tert.-C$_4$H$_9$ | 67–71 |
| 1248 | i-C$_3$H$_7$ | CH$_2$—CCl$_3$ | tert.-C$_4$H$_9$ | 72–75 |
| 1249 | i-C$_3$H$_7$ | 4-NHCOCH$_3$—C$_6$H$_4$ | tert.-C$_4$H$_9$ | 212–214 |
| 1250 | i-C$_3$H$_7$ | 2,4-Cl$_2$—C$_6$H$_3$ | tert.-C$_4$H$_9$ | 140–141 |
| 1251 | i-C$_3$H$_7$ | cyclooctanimino | tert.-C$_4$H$_9$ | oil, 1.37(d, 6H), 1.47(s, 9H), 1.28–1.93 (m; 10H), 2.54 (m; 4H), 3.44 (sept, 1H), 8.44 (bs; 1H, NH) |
| 1252 | i-C$_3$H$_7$ | (CH$_2$)$_2$O(CH$_2$)$_2$OCH$_3$ | tert.-C$_4$H$_9$ | oil, 1.34(d; 6H), 1.47 (s; 9H), 3.39 (s; 3H), 3.45 (sept; 1H), 3.60 (m; 4H), 3.84 and 4.50 (m; 4H), 8.94 (bs; 1H, NH) |
| 1253 | i-C$_3$H$_7$ | CH$_2$—CH$_2$—S—CH$_3$ | tert.-C$_4$H$_9$ | 46–48 |
| 1254 | i-C$_3$H$_7$ | Pyrid-2-yl | tert.-C$_4$H$_9$ | 155–163 |
| 1255 | i-C$_3$H$_7$ | CH$_2$—CH$_2$—Cl | tert.-C$_4$H$_9$ | 70–72 |
| 1263 | n-C$_4$H$_9$ | H | CH$_3$ | 146–149 |
| 1264 | n-C$_4$H$_9$ | H | i-C$_3$H$_7$ | 60–63 |
| 1265 | n-C$_4$H$_9$ | H | cyclo-C$_3$H$_5$ | 112–114 |
| 1266 | n-C$_4$H$_9$ | H | C$_6$H$_5$ | 145–150 |
| 1267 | n-C$_4$H$_9$ | H | tert.-C$_4$H$_9$ | 52–54 |
| 1268 | n-C$_4$H$_9$ | —N=C(CH$_3$)$_2$ | tert.-C$_4$H$_9$ | 58–62 |
| 1269 | n-C$_4$H$_9$ | —CH$_2$CCl$_3$ | tert.-C$_4$H$_9$ | oil 0.92 (t; 3H), 1.43 (m, 2H), 1.48(s; 9H), 1.74(m; 2H), 3.00(t; 2H), 5.01(s; 2H), 8.80(bs; 1H; NH) |
| 1270 | n-C$_4$H$_9$ | 2,6-Br$_2$-4-CN—C$_6$H$_2$ | tert.-C$_4$H$_9$ | 165–170 |
| 1271 | n-C$_4$H$_9$ | —CH$_2$—CH=CH$_2$ | tert.-C$_4$H$_9$ | oil 0.92(t; 3H), 1.41(m; 2H), 1.46(s; 9H), 1.66(m; 2H), 2.89(t; 2H), 4.88(d; 2H), 5.40(m; 2H), 6.01(m; 1H), 9.19(bs; 1H, NH) |
| 1272 | n-C$_4$H$_9$ | 2,4-dichlorobenzyl | tert.-C$_4$H$_9$ | 81–86 |
| 1273 | n-C$_4$H$_9$ | H | cyclopropylmethyl | 65–70 |
| 1274 | s-C$_4$H$_9$ | H | i-C$_3$H$_7$ | oil 0.92 (t, 3H), 1.34(d, 3H), 1.39(d; 6H), 1.76(m; 2H), 3.65(m; 1H), 4.32(m; 1H), 7.08(bs; 1H, NH) |
| 1275 | s-C$_4$H$_9$ | —N=C(CH$_3$)$_2$ | i-C$_3$H$_7$ | 80–84 |
| 1276 | s-C$_4$H$_9$ | H | cyclo-C$_3$H$_7$ | 78–85 |
| 1277 | s-C$_4$H$_9$ | —N=C(CH$_3$)$_2$ | cyclo-C$_3$H$_5$ | oil 0.70(m,; 2H), 0.90 (m; 2H), 0.92 (t; 3H), 1.34 (d; 3H), 1.79 (m; 2H), 2.14 and 2.18 (2s; 6H), 2.97 (m; 1H), 3.24 (m; 1H), 8.80 (bs, 1H, NH) |
| 1278 | s-C$_4$H$_9$ | succinimido | cyclo-C$_3$H$_5$ | 112–115 |
| 1279 | s-C$_4$H$_9$ | H | tert.-C$_4$H$_9$ | 93–95 |
| 1280 | s-C$_4$H$_9$ | —N=C(CH$_3$)$_2$ | tert.-C$_4$H$_9$ | oil 0.92 (t, 3H), 1.34 (d; 3H), 1.48 (s; 9H), 1.80 (m; 2H), |

TABLE 1-continued $$\underset{N\diagdown O}{\overset{R^1}{\|}}\diagup\overset{COOR^5}{CONHR^4}$$

| No. | R$^1$ | R$^5$ | R$^4$ | mp [°C.]/$^1$H-NMR (CDCl$_3$) [ppm] |
|---|---|---|---|---|
| | | | | 2.12 and 2.16 (2s; 6H), 3.26 (m, 1H), 8.29 (bs, 1H, NH) |
| 1281 | s-C$_4$H$_9$ | H | C$_6$H$_5$ | 117–120 |
| 1282 | s-C$_4$H$_9$ | —N=C(CH$_3$)$_2$ | C$_6$H$_5$ | oil, 0.93(t; 3H), 1.36 (d; 3H), 1.80 (m; 2H), 2.14 and 2.18 (2s; 6H), 3.28 (m; 1H), 7.10–7.80(m; 5H) 10.90(bs; 1H), NH) |
| 1283 | tert.-C$_4$H$_9$ | succinimido | i-C$_3$H$_7$ | 137–140 |
| 1284 | tert.-C$_4$H$_9$ | succinimido | 4-Cl—C$_6$H$_4$ | 238–242 |
| 1285 | tert.-C$_4$H$_9$ | succinimido | tert.-C$_4$H$_9$ | 144–146 |
| 1286 | tert.-C$_4$H$_9$ | —N=C(CH$_3$)$_2$ | tert.-C$_4$H$_9$ | 86–90 |
| 1287 | tert.-C$_4$H$_9$ | H | cyclo-C$_3$H$_5$ | 75–77 |
| 1288 | tert.-C$_4$H$_9$ | —N=C(CH$_3$)$_2$ | cyclo-C$_3$H$_5$ | 93–98 |
| 1290 | neo-C$_5$H$_{11}$ | H | CH$_3$ | 130–133 |
| 1291 | neo-C$_5$H$_{11}$ | H | i-C$_3$H$_7$ | 100–104 |
| 1292 | neo-C$_5$H$_{11}$ | H | cyclo-C$_3$H$_5$ | 133–136 |
| 1293 | neo-C$_5$H$_{11}$ | —N=C(CH$_3$)$_2$ | cyclo-C$_3$H$_5$ | 56–62 |
| 1294 | neo-C$_5$H$_{11}$ | H | tert.-C$_4$H$_9$ | 112–117 |
| 1295 | neo-C$_5$H$_{11}$ | —N=C(CH$_3$)$_2$ | tert.-C$_4$H$_9$ | 107–111 |
| 1296 | neo-C$_5$H$_{11}$ | H | C$_6$H$_5$ | 205–207 |
| 1297 | cyclo-C$_3$H$_5$ | succinimido | i-C$_3$H$_7$ | 131–133 |
| 1298 | cyclo-C$_3$H$_5$ | succinimido | tert.-C$_4$H$_9$ | 167–168 |
| 1299 | cyclo-C$_3$H$_5$ | succinimido | C$_6$H$_5$ | 168–170 |
| 1300 | cyclo-C$_3$H$_5$ | H | cyclo-C$_3$H$_5$ | 139–140 |
| 1301 | cyclo-C$_3$H$_5$ | —N=C(CH$_3$)$_2$ | cyclo-C$_3$H$_5$ | oil 0.80 (m; 8H), 2.02 and 2.04 (2s; 6H), 2.30 (m; 1H), 2.86 (m; 1H), 9.20 (d; 1H, NH) |
| 1302 | cyclo-C$_3$H$_5$ | —N=C(cyclo-C$_3$H$_5$)$_2$ | cyclo-C$_3$H$_7$ | 106–108 |
| 1303 | cyclo-C$_3$H$_5$ | H | cyclo-C$_5$H$_9$ | 106–109 |
| 1304 | cyclo-C$_3$H$_5$ | —N=C(CH$_3$)$_2$ | cyclo-C$_5$H$_9$ | 125–127 |
| 1305 | cyclo-C$_5$H$_9$ | H | C$_6$H$_5$ | 170–171 |
| 1306 | cyclo-C$_5$H$_9$ | H | cyclo-C$_3$H$_5$ | 118–120 |
| 1307 | cyclo-C$_5$H$_9$ | —N=C(CH$_3$)$_2$ | cyclo-C$_3$H$_5$ | 55–57 |
| 1308 | cyclo-C$_5$H$_9$ | —N=C(CH$_3$)$_2$ | CH$_3$ | 100–101 |
| 1309 | cyclo-C$_5$H$_9$ | H | CH$_3$ | 166–167 |
| 1310 | cyclo-C$_5$H$_9$ | H | tert.-C$_4$H$_9$ | 125–126 |
| 1311 | cyclo-C$_5$H$_9$ | —N=C(CH$_3$)$_2$ | tert.-C$_4$H$_9$ | 112–114 |
| 1312 | tetrahydro-pyran-3-yl | succinimido | C$_6$H$_5$ | 80 |
| 1313 | 2-CH$_3$O—C$_6$H$_4$ | H | tert.-C$_4$H$_9$ | 179–184 |
| 1314 | 2-CH$_3$O—C$_6$H$_4$ | H | cyclo-C$_4$H$_5$ | 177–180 |
| 1315 | 2,6F$_2$—C$_6$H$_3$ | H | tert.-C$_4$H$_9$ | 128–135 |
| 1316 | 2,6F$_2$—C$_6$H$_3$ | H | cyclo-C$_3$H$_5$ | 134–138 |
| 1317 | CH$_3$—O— | H | tert.-C$_4$H$_9$ | oil 1.52 (s; 9H), 4.12(s; 3H), 7.16(bs; 1H, NH) |
| 1318 | CH$_3$—O—CH$_2$ | H | tert.-C$_4$H$_9$ | 95–100 |
| 1319 | CH$_3$—O—CH$_2$ | H | cyclo-C$_3$H$_5$ | 90–95 |
| 1320 | CH$_3$—O—CH$_2$ | —N=C(CH$_3$)$_2$ | tert.-C$_4$H$_9$ | 65–70 |
| 1321 | CH$_3$—O—CH(CH$_3$)— | —N=C(CH$_3$)$_2$ | tert.-C$_4$H$_9$ | oil 1.45 (s; 9H) 1.60 (d; 3H), 2.16 and 2.18 (2s; 6H), 3.34 (s; 3H), 4.87 (quart.; 1H) 8.10(bs; 1H, NH) |
| 1322 | CH$_3$—O—CH(CH$_3$)— | H | tert.-C$_4$H$_9$ | 69–71 |
| 1323 | CH$_3$—O—CH(CH$_3$)— | 2,6-Br$_2$4-CN—C$_6$H$_2$ | tert.-C$_4$H$_9$ | 118–120 |
| 1324 | CH$_3$ | CH(CH$_3$)CO$_2$CH$_3$ | tert.-C$_4$H$_9$ | oil 1.46 (s; 9H) 2.54 (s; 3H) 3.82 (s; 3H), 5.40(quart.; 1H) 9.00(bs; 1H, NH) |
| 1325 | CH$_3$ | 2,6-Br$_2$-4-CN—C$_6$H$_2$ | tert.-C$_4$H$_9$ | 143–146 |

TABLE 1-continued $$\underset{N\diagdown O}{R^1}\!\!\!\!\!\!\!\!\!\!\!\!\!\!\!\!\!\!\!\!\!\!\!\!\!\!\!\!\!\underset{}{\overset{COOR^5}{\diagup}}\\\underset{}{\overset{CONHR^4}{\diagdown}}$$

| No. | R¹ | R⁵ | R⁴ | mp [°C.]/¹H-NMR (CDCl₃) [ppm] |
|---|---|---|---|---|
| 1326 | 1-methyl-3-methyl-pyrazol-5-yl | H | tert.-C₄H₉ | 168–170 |
| 1327 | 1-ethyl-4-methyl-pyrazol-5-yl | H | tert.-C₄H₉ | 157 |
| 1328 | 1-methyl-3-methyl-4-CO₂H-pyrazol-5-yl | H | tert.-C₄H₉ | 254 |
| 1329 | 1-methyl-3-methyl-pyrazol-5-yl | CH₃ | tert.-C₄H₉ | oil 1.5 (s, 9H) 3.8 (s; 3H), 3.9 (s; 3H), 6.5 (d; 1H), 7.6 (d; 1H), 8.7 (bs, 1H, NH) |
| 1330 | 1-ethyl-4-methyl-pyrazol-5-yl | CH₃ | tert.-C₄H₉ | 120–122° C. |
| 1331 | 3-methyl-4-CO₂CH₃-pyrazol-5-yl | CH₃ | tert.-C₄H₉ | oil, 1.5 (s; 9H), 3.7 (s; 3H), 3.8 (s; 3H), 3.9 (s; 3H), 8.0 (s; 1H), 9.2 (bs, 1H, NH) |
| 1332 | 2-thienyl | H | tert.-C₄H₉ | |
| 1333 | 2-thienyl | —N=C(CH₃)₂ | tert.-C₄H₉ | |
| 1334 | 2-furyl | H | tert.-C₄H₉ | |
| 1335 | 2-furyl | —N=C(CH₃)₂ | tert.-C₄H₉ | |
| 1336 | pyrid-2-yl | H | tert.-C₄H₉ | |
| 1337 | pyrid-2-yl | —N=C(CH₃)₂ | tert.-C₄H₉ | |
| 1338 | pyrid-3-yl | H | tert.-C₄H₉ | |
| 1339 | pyrid-3-yl | —N=C(CH₃)₂ | tert.-C₄H₉ | |
| 1340 | pyrid-4-yl | H | tert.-C₄H₉ | |
| 1341 | pyrid-4-yl | —N=C(CH₃)₂ | tert.-C₄H₉ | |
| 1342 | 4-F—C₆H₄—CH₂ | H | tert.-C₄H₉ | |
| 1343 | 4-F—C₆H₄—CH₂ | —N=C(CH₃)₂ | tert.-C₄H₉ | |

TABLE 1-continued

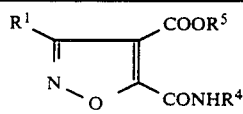

| No. | R¹ | R⁵ | R⁴ | mp [°C.]/¹H-NMR (CDCl₃) [ppm] |
|---|---|---|---|---|
| 1344 | $CH_3$ | $n-C_4H_9$ | $tert.-C_4H_9$ | |
| 1345 | $CH_3$ | $C_6H_5$ | $tert.-C_4H_9$ | |
| 1346 | $CH_3$ | $tert.-C_4H_9$ | $tert.-C_4H_9$ | |
| 1347 | $C_2H_5$ | $n-C_4H_9$ | $tert.-C_4H_9$ | |
| 1348 | $C_2H_5$ | $C_6H_5$ | $tert.-C_4H_9$ | |
| 1349 | $i-C_3H_7$ | $n-C_4H_9$ | $tert.-C_4H_9$ | |
| 1350 | $i-C_3H_7$ | $C_6H_5$ | $tert.-C_4H_9$ | |
| 1351 | $i-C_3H_7$ | cyclopentanimino | $tert.-C_4H_9$ | 113–115 |

TABLE 2

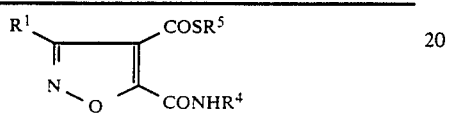

| No. | R¹ | R⁵ | R⁴ | mp [°C.]/¹H-NMR (CDCl₃) [ppm] |
|---|---|---|---|---|
| 2001 | $CH_3$ | $n-C_4H_9$ | $tert.-C_4H_9$ | |
| 2002 | $CH_3$ | $C_6H_5$ | $tert.-C_4H_9$ | |
| 2003 | $CH_3$ | $tert.-C_4H_9$ | $tert.-C_4H_9$ | oil: 1.46 (s: 9H) 1.60(s: 9H). 2.50 (s: 3H), 7.94 (bs: 1H, NH) |
| 2004 | $C_2H_5$ | $n-C_4H_9$ | $tert.-C_4H_9$ | |
| 2005 | $C_2H_5$ | $C_6H_5$ | $tert.-C_4H_9$ | |
| 2006 | $i-C_3H_7$ | $C_6H_5$ | $tert.-C_4H_9$ | |
| 2007 | $i-C_3H_7$ | $n-C_4H_9$ | $tert.-C_4H_9$ | |

TABLE 3

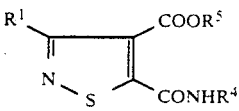

| No. | R¹ | R⁵ | R⁴ | mp [°C.]/H-NMR (CDCl₃) [ppm] |
|---|---|---|---|---|
| 3001 | $CH_3$ | H | $i-C_3H_7$ | 153–154 |
| 3002 | $CH_3$ | H | $tert.-C_4H_9$ | 158–159 |
| 3003 | $CH_3$ | H | $C_6H_5$ | 178–183 |
| 3004 | $CH_3$ | H | $4-Cl-C_6H_4$ | 231 |
| 3005 | $CH_3$ | H | $3-CF_3-C_6H_4$ | 221–223 |
| 3006 | $C_2H_5$ | H | $i-C_3H_7$ | 138–140 |
| 3007 | $C_2H_5$ | $CH_3$ | $i-C_3H_7$ | 55–56 |
| 3008 | $C_2H_5$ | H | $tert.-C_4H_9$ | 155–157 |
| 3009 | $C_2H_5$ | $CH_3$ | $tert.-C_4H_9$ | 39 |
| 3010 | $C_2H_5$ | H | $C_6H_5$ | 164 |
| 3011 | $C_2H_5$ | $CH_3$ | $C_6H_5$ | 130–131 |
| 3012 | $C_2H_5$ | H | $4-Cl-C_6H_4$ | 202–204 |
| 3013 | $C_2H_5$ | $CH_3$ | $4-Cl-C_6H_4$ | 158–159 |
| 3014 | $C_2H_5$ | H | $3-CF_3-C_6H_4$ | 191–195 |
| 3015 | $C_2H_5$ | $CH_3$ | $3-CF_3-C_6H_4$ | 84 |
| 3016 | $i-C_3H_7$ | H | $i-C_3H_7$ | 160–162 |
| 3017 | $i-C_3H_7$ | $CH_3$ | $i-C_3H_7$ | 90–91 |
| 3018 | $i-C_3H_7$ | H | $tert.-C_4H_9$ | 178–179 |
| 3019 | $i-C_3H_7$ | $CH_3$ | $tert.-C_4H_9$ | 38–41 |
| 3020 | $i-C_3H_7$ | H | $C_6H_5$ | 171–172 |
| 3021 | $i-C_3H_7$ | $CH_3$ | $C_6H_5$ | 92–93 |
| 3022 | $i-C_3H_7$ | H | $4-Cl-C_6H_4$ | 185–186 |
| 3023 | $i-C_3H_7$ | $CH_3$ | $4-Cl-C_6H_4$ | 92–93 |
| 3024 | $i-C_3H_7$ | H | $3-CF_3-C_6H_4$ | 177–179 |
| 3025 | $i-C_3H_7$ | $CH_3$ | $3-CF_3-C_6H_4$ | 37–45 |
| 3026 | $C_6H_5$ | H | $i-C_3H_7$ | 144 |
| 3027 | $C_6H_5$ | $CH_3$ | $i-C_3H_7$ | 98–100 |
| 3028 | $C_6H_5$ | H | $tert.-C_4H_9$ | 209 |
| 3029 | $C_6H_5$ | $CH_3$ | $tert.-C_4H_9$ | 130–131 |

TABLE 3-continued

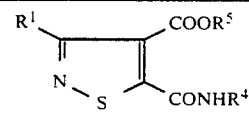

| No. | R¹ | R⁵ | R⁴ | mp [°C.]/H-NMR (CDCl₃) [ppm] |
|---|---|---|---|---|
| 3030 | $C_6H_5$ | H | $C_6H_5$ | 204 |
| 3031 | $C_6H_5$ | $CH_3$ | $C_6H_5$ | 100–101 |
| 3032 | $C_6H_5$ | H | $4-Cl-C_6H_4$ | 209 |
| 3033 | $C_6H_5$ | $CH_3$ | $4-Cl-C_6H_4$ | 157–158 |
| 3034 | $C_6H_5$ | H | $3-CF_3-C_6H_4$ | 217 |
| 3035 | $C_6H_5$ | $CH_3$ | $3-CF_3-C_6H_4$ | 131–132 |
| 3036 | $i-C_3H_7$ | succinimido | $i-C_3H_7$ | 98–100 |
| 3037 | $i-C_3H_7$ | succinimido | $tert.-C_4H_9$ | 75–76 |
| 3038 | $i-C_3H_7$ | $Na^\oplus$ | $tert.-C_4H_9$ | 300 |
| 3039 | $i-C_3H_7$ | $K^\oplus$ | $tert.-C_4H_9$ | 110 |
| 3040 | $i-C_3H_7$ | $Na^\oplus$ | $C_6H_5$ | 330 |
| 3041 | $i-C_3H_7$ | $K^\oplus$ | $C_6H_5$ | 300 |
| 3042 | $i-C_3H_7$ | $H_3N^\oplus-CH(CH_3)_2$ | $C_6H_5$ | 154–157 |
| 3043 | $i-C_3H_7$ | $H_3N^\oplus-CH_2-CH_2-OH$ | $C_6H_5$ | 162–164 |
| 3044 | $i-C_3H_7$ | succinimido | $C_6H_5$ | 161 |
| 3045 | $CH_3$ | $-N=C(CH_3)_2$ | $tert.-C_4H_9$ | 97–98 |

Other compounds, for instance, having the general structure

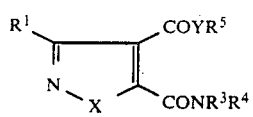

may be prepared analogously in which X and Y are oxygen or sulfur, e.g.,

R¹ is a radical from the group Q1 to Q61,
R⁵ is a radical from the group M1 to M78,
R³ is a radical from the group $P_1-P_{11}$
R⁴ is a radical from the group L1 to L195, and
the radicals X, Y, P, Q, M and L may be combined at will.

R¹, R⁵, R³ and R⁴ may be for example denote the following radicals:

| Comp. No. | R¹ | Comp. No. | R¹ |
|---|---|---|---|
| Q1 | H | Q24 | tetrahydropyran-3-yl |
| Q2 | CH₃ | | |
| Q3 | C₂H₅ | Q25 | tetrahydropyran-3-yl |
| Q4 | n-C₃H₇ | Q26 | C₆H₅ |
| Q5 | i-C₃H₇ | Q27 | 2-F—C₆H₄ |
| Q6 | n-C₄H₉ | Q28 | 3-F—C₆H₄ |
| Q7 | i-C₄H₉ | Q29 | 4-F—C₆H₄ |
| Q8 | s-C₄H₉ | Q30 | 2-Cl—C₆H₄ |
| Q9 | tert.-C₄H₉ | Q31 | 3-Cl—C₆H₄ |
| Q10 | cyclo-C₃H₅ | Q32 | 4-Cl—C₆H₄ |
| Q11 | cyclo-C₄H₇ | Q33 | 2-CH₃—C₆H₄ |
| Q12 | cyclo-C₅H₉ | Q34 | 3-CH₃—C₆H₄ |
| Q13 | cyclo-C₆H₁₁ | Q35 | 4-CH₃—C₆H₄ |
| Q14 | cyclo-C₇H₁₃ | Q36 | 2-CF₃—C₆H₄ |
| Q15 | cyclo-C₈H₁₅ | Q37 | 3-CF₃—C₆H₄ |
| Q16 | CF₃ | Q38 | 4-CF₃—C₆H₄ |
| Q17 | CH₂OCH₃ | Q39 | 2-OCH₃—C₆H₄ |
| Q18 | CH(CH₃)OCH₃ | Q40 | 3-OCH₃—C₆H₄ |
| Q19 | CH(CH₃)CH₂OCH₃ | Q41 | 4-OCH₃—C₆H₄ |
| Q20 | CH₂OC₂H₅ | Q42 | 4-OCF₃—C₆H₄ |
| Q21 | tetrahydrofur-2-yl | Q43 | 4-SCH₃—C₆H₄ |
| Q22 | tetrahydrofur-2-yl | Q44 | 4-SCF₃—C₆H₄ |
| Q23 | tetrahydrofur-2-yl | Q45 | 4-NO₂—C₆H₄ |
| Q47 | neo-C₅H₁₁ | Q46 | 4-CN—C₆H₄ |
| Q48 | CH₃O | Q56 | 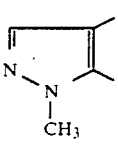 |
| Q49 | C₂H₅O | Q57 | 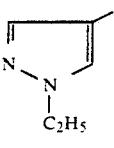 |
| Q50 | C₆H₅—CH₂ | Q58 | 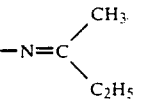 |
| Q51 | 4-F—C₆H₄—CH₂ | Q59 | pyrid-2-yl |
| Q51 | 4-CH₃—C₆H₄—CH₂— | Q60 | pyrid-3-yl |
| Q52 | 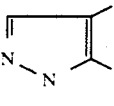 | Q61 | pyrid-4-yl |
| Q53 | 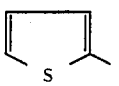 | Q62 | 2,6-F₂—C₆H₃ |
| Q54 | 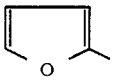 | | |
| Q55 | 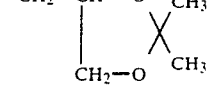 | | |

| Comp. No. | R⁵ |
|---|---|
| M1 | H |
| M2 | CH₃ |
| M3 | C₂H₅ |
| M4 | n-C₃H₇ |
| M5 | i-C₃H₇ |
| M6 | n-C₄H₉ |
| M7 | s-C₄H₉ |
| M8 | t-C₄H₉ |
| M9 | CH(CH₃)C₆H₁₃ |
| M10 | CH₂CH₂OCH₃ |
| M11 | CH₂CH₂OC₂H₅ |
| M12 | succinimido |
| M13 | Li⊕ |
| M14 | Na⊕ |
| M15 | K⊕ |
| M16 | NH₄⊕ |
| M17 | H₃N⊕i-C₃H₇ |
| M18 | H₂N⊕(i-C₃H₇)₂ |
| M19 | H₃N⊕CH₂CH₂OH |
| M20 | CH₂CH=CH₂ |
| M21 | CH₂—C(CH₃)=CH₂ |
| M22 | CH₂—C(Cl)=CH₂ |
| M23 | CH₂—C≡CH |
| M24 | CH₂—C≡C—CH₂OH |
| M25 | —N=C(CH₃)₂ |
| M26 | —N=C(C₂H₅)₂ |
| M27 | CH₂—CH₂—N(CH₃)₂ |
| M28 | CH₂—CH₂—N(C₂H₅)₂ |
| M29 | CH₂—CH₂N⊕(CH₃)₃I⊖ |
| M30 | CH₂—CF₃ |
| M31 | phenyl |
| M32 | phenylethyl |
| M33 | CH₂—CH₂—Si(CH₃)₃ |
| M34 | CH₂—CH₂—ON=C(CH₃)₂ |
| M35 | CH₂—PO(OC₂H₅)₂ |
| M36 | CH(CH₃)CH(OCH₃)₂ |
| M37 | CH₂—CON(C₂H₅)₂ |
| M38 | N(C₂H₅)₂ |
| M39 | CH₂—OCH₂—C₆H₅ |
| M40 | CH(COOCH₃)₂ |
| M41 | —N=C(cyclo-C₃H₅)₂ |
| M42 | 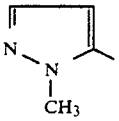 |
| M43 | cyclohexanimino |
| M44 | cyclooctanimino |
| M45 | CH₂—CH₂—Cl |
| M46 | CH₂—CH₂—CN |
| M47 | CH₂—CCl₃ |
| M48 | pyrid-3-ylmethyl |
| M49 | thien-2-yl-methyl |
| M50 | 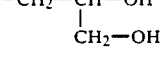 |
| M51 | 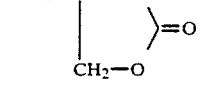 |
| M52 | 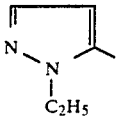 |
| M53 | —CH(C₆H₅)COOCH₃ |
| M54 | cyclo-C₆H₁₁ |
| M55 | —CH₂—OCH₂—C₆H₅ |
| M56 | tetrahydropyran-2-yl |
| M57 | tetrahydrofur-2-yl |
| M58 | (4-bromobenzoyl)methyl |
| M59 | (4-methoxybenzoyl)methyl |
| M60 | —CH(COOCH₃)₂ |
| M61 | phthalimidomethyl |

-continued

| Comp. No. | R⁵ |
|---|---|
| M62 | fur-2-ylmethyl |
| M63 | tetrahydrofur-2-yl-methyl |
| M64 | pyrid-2-ylmethyl |
| M65 | pyrid-4-ylmethyl |
| M66 | pyrid-3-yl-methyl |
| M67 | thien-2-yl-methyl |
| M68 | —CH(C₆H₅)COOCH₃ |
| M69 | piperidino |
| M70 | phthalimido |
| M71 | ![structure: -N-N=N fused to benzene ring (benzotriazol-1-yl)] |
| M72 | —N=CH—C₆H₅ |
| M73 | —N=CH-(furan-2-yl) |
| M74 | 2-NO₂-4-F—C₆H₃ |
| M75 | 3,5-(CF₃)₂—C₆H₃ |
| M76 | CH₂—CH₂—S—CH₃ |
| M77 | 4-NHCOCH₃—C₆H₄ |
| M78 | 2,4-dichlorobenzyl |

| Comp. No. | R³ | Comp. No. | R³ |
|---|---|---|---|
| P1 | H | P12 | CH₂OC₂H₅ |
| P2 | CH₃ | P13 | CH₂CH₂OCH₃ |
| P3 | C₂H₅ | P14 | CH₂SCH₃ |
| P4 | n-C₃H₇ | P15 | CH₂SC₂H₅ |
| P5 | i-C₃H₇ | P16 | CH₂CH₂SCH₃ |
| P6 | n-C₄H₉ | P17 | CH₂-CH₂-N(CH₃)₂ |
| P7 | s-C₄H₉ | P18 | CH₂-CH₂-N(C₂H₅)₂ |
| P8 | t-C₄H₉ | P19 | cyclo-C₃H₅ |
| P9 | CH₂-CH₂OH | P20 | cyclo-C₆H₁₁ |
| P10 | CH₂-CH₂Cl | P21 | 1-methyl-cyclo-C₆H₁₀ |
| P11 | CH₂OCH₃ | | |

| Comp. No. | R⁴ |
|---|---|
| L1 | H |
| L2 | CH₃ |
| L3 | C₂H₅ |
| L4 | n-C₃H₇ |
| L5 | i-C₃H₇ |
| L6 | n-C₄H₉ |
| L7 | i-C₄H₉ |
| L8 | sec-C₄H₉ |
| L9 | tert.-C₄H₉ |
| L10 | n-C₅H₁₁ |
| L11 | —CH(CH₃)C₃H₇ |
| L12 | —CH(C₂H₅)C₂H₅ |
| L13 | n-C₆H₁₃ |
| L14 | —CH(CH₃)C₄H₉ |
| L15 | —CH(C₂H₅)C₃H₇ |
| L16 | n-C₇H₁₅ |
| L17 | —CH(CH₃)C₅H₁₁ |
| L18 | —CH(C₂H₅)C₄H₉ |
| L19 | n-C₈H₁₇ |
| L20 | —CH(CH₃)C₆H₁₃ |
| L21 | —CH(C₂H₅)C₅H₁₁ |
| L22 | —C(CH₃)₂CH₂C(CH₃)₃ |
| L23 | cyclo-C₃H₅ |
| L24 | cyclo-C₄H₇ |
| L25 | cyclo-C₅H₉ |
| L26 | cyclo-C₆H₁₁ |
| L27 | cyclo-C₇H₁₃ |
| L28 | cyclo-C₈H₁₅ |
| L29 | 1-methylcyclohexyl |
| L30 | 1-ethylcyclohexyl |
| L31 | 3,5-dimethylcyclohexyl |
| L32 | 3-trifluoromethylcyclohexyl |
| L33 | tetrahydropyran-4-yl |
| L34 | 4-methyl-tetrahydropyran |
| L35 | 4-methyl-tetrahydropyran-4-yl |
| L36 | —CH₂—CH=CH₂ |
| L37 | —CH(CH₃)CH=CH₂ |
| L38 | —C(CH₃)₂CH=CH₂ |
| L39 | —C(CH₃, C₂H₅)CH=CH₂ |
| L40 | —C(CH₃)₂—C₂H₅ |
| L41 | —C(CH₃, C₂H₅)C₂H₅ |
| L42 | —C(CH₃)₂C₃H₇ |
| L43 | —C(CH₃)₂cycloC₆H₁₁ |
| L44 | —CH₂—C(CH₃)=CH₂ |
| L45 | —CH₂CH=CHCH₃ |
| L46 | —CH(CH₃)CH=CHCH₃ |
| L47 | —C(CH₃)₂CH=CHCH₃ |
| L48 | —CH₂C≡CH |
| L49 | —CH(CH₃)C≡CH |
| L50 | —C(CH₃)₂C≡CH |
| L51 | —C(CH₃, C₂H₅)C≡CH |
| L52 | —C(C₂H₅)₂C≡CH |
| L53 | —CH₂C≡CCH₃ |
| L54 | —CH(CH₃)C≡CCH₃ |
| L55 | —C(CH₃)₂C≡CCH₃ |
| L56 | —CH₂C₆H₅ |
| L57 | —CH(CH₃)C₆H₅ |
| L58 | —C(CH₃)₂C₆H₅ |
| L59 | —CH₂CH₂C₆H₅ |
| L60 | —CH₂CH₂SCH₃ |
| L61 | —CH(CH₃)CH₂SCH₃ |
| L62 | —C(CH₃)₂CH₂SCH₃ |
| L63 | —CH₂CH₂CH₂SCH₃ |
| L64 | —CH₂CH₂Cl |
| L65 | —CH(CH₃)CH₂Cl |
| L66 | —C(CH₃)₂CH₂Cl |
| L67 | —CH₂CH₂OCH₃ |
| L68 | —CH(CH₃)CH₂OCH₃ |
| L69 | —C(CH₃)₂CH₂OCH₃ |
| L70 | —CH₂CH₂N(CH₃)₂ |
| L71 | —CH₂CH₂N(C₂H₅)₂ |
| L72 | —CH₂CH₂CH₂OCH₃ |
| L73 | —CH₂CH₂CH₂N(CH₃)₂ |
| L74 | —CH₂CH₂CH₂N(C₂H₅)₂ |
| L75 | 2-CH₃—C₆H₄ |
| L76 | 3-CH₃—C₆H₄ |
| L77 | 4-CH₃—C₆H₄ |
| L78 | 2-C₂H₅—C₆H₄ |
| L79 | 3-C₂H₅—C₆H₄ |
| L80 | 4-C₂H₅—C₆H₄ |
| L81 | 3-tert.-C₄H₉—C₆H₄ |
| L82 | 4-tert.-C₄H₉—C₆H₄ |
| L83 | 2,3-(CH₃)₂—C₆H₃ |
| L84 | 2,4-(CH₃)₂—C₆H₃ |
| L85 | 2,5-(CH₃)₂—C₆H₃ |
| L86 | 2,6-(CH₃)₂—C₆H₃ |
| L87 | 3,4-(CH₃)₂—C₆H₃ |
| L88 | 3,5-(CH₃)₂—C₆H₃ |
| L89 | 2,3,4-(CH₃)₃—C₆H₂ |
| L90 | 2,3,5-(CH₃)₃—C₆H₂ |
| L91 | 2,4,5-(CH₃)₃—C₆H₂ |
| L92 | 2,4,6-(CH₃)₃—C₆H₂ |
| L93 | 3,4,5-(CH₃)₃—C₆H₂ |
| L94 | 2-CF₃—C₆H₄ |
| L95 | 3-CF₃—C₆H₄ |
| L96 | 4-CF₃—C₆H₄ |
| L97 | 2-F—C₆H₄ |
| L98 | 3-F—C₆H₄ |
| L99 | 4-F—C₆H₄ |
| L100 | 2-Cl—C₆H₄ |
| L101 | 3-Cl—C₆H₄ |
| L102 | 4-Cl—C₆H₄ |
| L103 | 2-Br—C₆H₄ |
| L104 | 3-Br—C₆H₄ |
| L105 | 4-Br—C₆H₄ |
| L106 | 2,3-F₂—C₆H₃ |
| L107 | 2,4-F₂—C₆H₃ |
| L108 | 2,5-F₂—C₆H₃ |
| L109 | 2,6-F₂—C₆H₃ |
| L110 | 2,3-Cl₂—C₆H₃ |

| Comp. No. | R$^4$ |
|---|---|
| L111 | 2,4-Cl$_2$—C$_6$H$_3$ |
| L112 | 2,5-Cl$_2$—C$_6$H$_3$ |
| L113 | 2,6-Cl$_2$—C$_6$H$_3$ |
| L114 | 3,4-Cl$_2$—C$_6$H$_3$ |
| L115 | 3,5-Cl$_2$—C$_6$H$_3$ |
| L116 | 2,3,4-Cl$_3$—C$_6$H$_2$ |
| L117 | 2,3,5-Cl$_3$—C$_6$H$_2$ |
| L118 | 2,4,6-Cl$_3$—C$_6$H$_2$ |
| L119 | 3,4,5-Cl$_3$—C$_6$H$_2$ |
| L120 | 2-CN—C$_6$H$_4$ |
| L121 | 3-CN—C$_6$H$_4$ |
| L122 | 4-CN—C$_6$H$_4$ |
| L123 | 2-OCH$_3$—C$_6$H$_4$ |
| L124 | 3-OCH$_3$—C$_6$H$_4$ |
| L125 | 4-OCH$_3$—C$_6$H$_4$ |
| L126 | 2-OC$_2$H$_5$—C$_6$H$_4$ |
| L127 | 3-OC$_2$H$_5$—C$_6$H$_4$ |
| L128 | 4-OC$_2$H$_5$—C$_6$H$_4$ |
| L129 | 2-O-n-C$_3$H$_7$—C$_6$H$_4$ |
| L130 | 3-O-n-C$_3$H$_7$—C$_6$H$_4$ |
| L131 | 4-O-n-C$_3$H$_7$—C$_6$H$_4$ |
| L132 | 2-O-i-C$_3$H$_7$—C$_6$H$_4$ |
| L133 | 3-O-i-C$_3$H$_7$—C$_6$H$_4$ |
| L134 | 4-O-i-C$_3$H$_7$—C$_6$H$_4$ |
| L135 | 2,3-(OCH$_3$)$_2$—C$_6$H$_3$ |
| L136 | 2,4-(OCH$_3$)$_2$—C$_6$H$_3$ |
| L137 | 2,5-(OCH$_3$)$_2$—C$_6$H$_3$ |
| L138 | 2,6-(OCH$_3$)$_2$—C$_6$H$_3$ |
| L139 | 3,4-(OCH$_3$)$_2$—C$_6$H$_3$ |
| L140 | 3,5-(OCH$_3$)$_2$—C$_6$H$_3$ |
| L141 | 3,4,5-(OCH$_3$)$_3$—C$_6$H$_2$ |
| L142 | 2-OCF$_3$—C$_6$H$_4$ |
| L143 | 3-OCF$_3$—C$_6$H$_4$ |
| L144 | 4-OCF$_3$—C$_6$H$_4$ |
| L145 | 2-OCF$_2$CHF$_2$—C$_6$H$_4$ |
| L146 | 3-OCF$_2$CHF$_2$—C$_6$H$_4$ |
| L147 | 4-OCF$_3$CHF$_2$—C$_6$H$_4$ |
| L148 | 2-SCH$_3$—C$_6$H$_4$ |
| L149 | 3-SCH$_3$—C$_6$H$_4$ |
| L150 | 4-SCH$_3$—C$_6$H$_4$ |
| L151 | 2-SC$_2$H$_5$—C$_6$H$_4$ |
| L152 | 3-SC$_2$H$_5$—C$_6$H$_4$ |
| L153 | 4-SC$_2$H$_5$—C$_6$H$_4$ |
| L154 | 2-S-i-C$_3$H$_7$—C$_6$H$_4$ |
| L155 | 3-S-i-C$_3$H$_7$—C$_6$H$_4$ |
| L156 | 4-S-i-C$_3$H$_7$—C$_6$H$_4$ |
| L157 | 2,4-(SCH$_3$)$_2$—C$_6$H$_3$ |
| L158 | 2-SCF$_3$—C$_6$H$_4$ |
| L159 | 3-SCF$_3$—C$_6$H$_4$ |
| L160 | 4-SCF$_3$—C$_6$H$_4$ |
| L161 | 2-NO$_2$—C$_6$H$_4$ |
| L162 | 3-NO$_2$—C$_6$H$_4$ |
| L163 | 4-NO$_2$—C$_6$H$_4$ |
| L164 | 2,3-(NO$_2$)$_2$—C$_6$H$_3$ |
| L165 | 2,4-(NO$_2$)$_2$—C$_6$H$_3$ |
| L166 | 2,5-(NO$_2$)$_2$—C$_6$H$_3$ |
| L167 | 2,6-(NO$_2$)$_2$—C$_6$H$_3$ |
| L168 | 3,4-(NO$_2$)$_2$—C$_6$H$_3$ |
| L169 | 3,5-(NO$_2$)$_2$—C$_6$H$_3$ |
| L170 | 2-CHO—C$_6$H$_4$ |
| L171 | 3-CHO—C$_6$H$_4$ |
| L172 | 4-CHO—C$_6$H$_4$ |
| L173 | 2-C(=O)CH$_3$—C$_6$H$_4$ |
| L174 | 3-C(=O)CH$_3$—C$_6$H$_4$ |
| L175 | 4-C(=O)CH$_3$—C$_6$H$_4$ |
| L176 | 2-C(=O)C$_2$H$_5$—C$_6$H$_4$ |
| L177 | 3-C(=O)C$_2$H$_5$—C$_6$H$_4$ |
| L178 | 4-C(=O)C$_2$H$_5$—C$_6$H$_4$ |
| L179 | 2-C(=O)-n-C$_3$H$_7$—C$_6$H$_4$ |
| L180 | 3-C(=O)-n-C$_3$H$_7$—C$_6$H$_4$ |
| L181 | 4-C(=O)-n-C$_3$H$_7$—C$_6$H$_4$ |
| L182 | 2-C(=O)CF$_3$—C$_6$H$_4$ |
| L183 | 3-C(=O)CF$_3$—C$_6$H$_4$ |
| L184 | 4-C(=O)CF$_3$—C$_6$H$_4$ |
| L185 | 1-naphthyl |
| L186 | 2-naphthyl |
| L187 | C$_6$H$_5$ |
| L188 | piperidino |
| L189 | tetrahydrofur-3-yl |
| L190 | thiazol-2-yl |
| L191 | 5-methyl-thiazol-2-yl |
| L192 | 5-ethyl-thiazol-2-yl |
| L193 | 5-n-propyl-thiazol-2-yl |
| L194 | 4-methyl-5-carboxy-thiazol-2-yl |
| L195 | cyclopropylmethyl |

The compounds Ia, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsion, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations are as follows:

I. 90 parts by weight of compound no. 1006 is mixed with 10 parts by weight of N-methyl-alpha-pyrrolidone. A mixture is obtained which is suitable for application in the form of very fine drops.

II. 20 parts by weight of compound no. 1006 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1002 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.2% by weight of the active ingredient.

IV. 20 parts by weight of compound no. 1049 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3038 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1075 is intimately mixed with 97 parts by weight of particulate kaolin. A dust is obtained containing 3% by weight of the active ingredient.

VII. 30 parts by weight of compound no. 1220 is intimately mixed with a mixture consisting of 92 parts by weight of powered silica gel and 8 parts by weight of paraffin oil which has been sprayed onto the surface of this silica gel. A formulation of the active ingredient is obtained having good adherence.

VIII. 20 parts of compound no. 1026 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The formulations contain from 0.1 to 95, and preferably 0.5 to 90, % by weight of active ingredient.

The active ingredients may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare.

In view of the spectrum of unwanted plants which can be combated, the tolerance of the novel compounds by crop plants, and in view of the number of application methods possible, the compounds of the formula Ia, or agents containing them, may be used in a further large number of crops for removing unwanted plants. The following crops are given by way of example:

| Botanical name | Common name |
| --- | --- |
| *Allium cepa* | onions |

-continued

| Botanical name | Common name |
| --- | --- |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | swedes |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica (Coffea canephora, Coffea liberica)* | coffee plants |
| *Cucumis melo* | melons |
| *Cucumis sativus* | cucumbers |
| *Cynodon dactylon* | Bermudagrass |
| *Elais guineensis* | oil palms |
| *Fragaria vesca* | strawberries |
| *Glycine max* | soybeans |
| *Gossypium hirsutum (Gossypium arboreum, Gossypium herbaceum, Gossypium vitifolium)* | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculanta* | cassava |
| *Medicago sativa* | alfalfa (lucerne) |
| *Mentha piperita* | peppermint |
| *Musa* spp. | banana plants |
| *Nicotiana tabacum (N. rustica)* | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. vulgare) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | Wheat |
| *Triticum durum* | durum wheat |
| *Vaccinium corymbosum* | blueberries |
| *Vaccinium vitis-idaea* | cranberries |
| *Vicia faba* | tick beans |

| Botanical name | Common name |
| --- | --- |
| *Vigna sinensis* (V. unguiculata) | cow peas |
| *Vitis vinifera* | grapes |
| *Zea mays* | Indian corn, sweet corn, maize |

To increase the spectrum of action and to achieve synergistic effects, the isoxazole-(isothiazole)-5-carboxamides of the formula Ia may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, sulfonylureas, imidazolinones, (hetero)aryloxyphenylpropionic acids and salts, esters and amides thereof, etc.

It may also be useful to apply the compounds of the formula Ia, either alone or in combination with other herbicides, in admixture with other crop protecting agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

USE EXAMPLES

The action of the isoxazole-(isothiazole)-5-carboxamides of the formula Ia on plant growth is demonstrated in greenhouse experiments.

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. The application rate was 0.5 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For postemergence treatment, either plants which had been sown in the pots and grown there were selected, or they were cultivated separately as seedlings and transplanted to the pots a few days before being treated.

The plants were grown, depending on growth form, to a height of 3 to 15 cm before being treated with the active ingredients, which were suspended or emulsified in water as vehicle, and sprayed through finely distributing nozzles. The application rates for postemergence treatment were 1.0 and 3.0 kg/ha.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0, to 100, 100 denoting nonemergence or complete destruction of at least the visible plant parts, and 0 denoting no damage or normal growth.

The plants used in the greenhouse experiments were Abutilon theophrasti, Centaurea cyanus, Chenopodium album, Chrysanthemum coronarium, Echinochloa crusgalli, Galium aparine, Ipomoea spp., Lolium multiflorum, Mentha piperita, Mercurialis annua, Solanum nigrum, Triticum aestivum, Viola spp. and Zea mays.

Active ingredient no. 1006 selected by way of example combated unwanted plants excellently on preemergence application of 3.0 kg/ha.

For example compounds nos. 1004, 1014, 3018, 1026, 1006, 1049 and 1022 had, on postemergence application of 1 to 3 kg/ha, a herbicidal action on a broad spectrum of unwanted plants. Compounds nos. 1075 and 3038 also has a very good herbicidal action on broadleaved plants and were tolerated by Indian corn. Compound no. 211 had an excellent herbicidal action and was tolerated by wheat.

We claim:

1. Isoxazole-5-carboxamides of the formula I

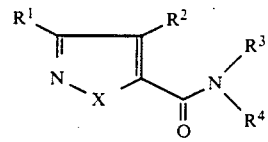

where

X is oxygen,

R$^1$ is: hydrogen;

C$_1$-C$_{10}$-alkyl which is unsubstituted or substituted by C$_1$-C$_3$-alkoxy, C$_1$-C$_3$-haloalkoxy, halogen, cyano or phenyl, which in turn may be substituted by halogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, cyano, or nitro;

C$_1$-C$_4$-alkoxy;

C$_3$-C$_8$-cycloalkyl which is unsubstituted or substituted by C$_1$-C$_4$-alkyl or halogen;

phenyl which is unsubstituted or substituted by C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, halogen, nitro or cyano;

a 5- or 6-membered heterocyclic radical which is unsubstituted or substituted by C$_1$-C$_4$-alkyl, carboxyl or C$_1$-C$_4$-alkoxycarbonyl, said heterocyclic radical being attached via carbon and selected from the group consisting of tetrahydrofuryl, tetrahydropyranyl, pyridyl, thienyl, furyl and pyrazolyl;

R$^2$ is: formyl; 4,5-dihydrooxazol-2-yl; or a radical of the formula —COYR$^5$ or —CONR$^6$R$^7$, where Y is oxygen or sulfur;

R$^5$ is: hydrogen;

C$_1$-C$_8$-alkyl which is unsubstituted or substituted by C$_1$-C$_4$-alkoxy, C$_1$-C$_4$-alkoxy-C$_1$-C$_4$-alkoxy, halogen, cyano, hydroxy, trimethylsilyl, C$_1$-C$_4$- alkylthio, $C_1$-$C_4$-alkylamino, $C_1$-$C_4$-dialkylamino, $C_1$-$C_4$-alkylsulfinyl, $C_1$-$C_4$-alkylsulfonyl, carboxyl, $C_1$-$C_4$-alkoxycarbonyl, $C_1$-$C_4$-dialkyloaminocarbonyl, $C_1$-$C_4$-dialkoxyphosphonyl, 2-propane-iminooxy, thienyl, furyl, tetrahydrofuryl, phthalimido, pyridyl, benzyloxy, benzoyl which is unsubstituted or substituted by $C_1$-$C_4$-alkyl, $C_1$-$C_3$-alkoxy or halogen; and phenyl which is unsubstituted or substituted by $C_1$-$C_4$-alkyl, $C_1$-$C_4$-alkoxy, $C_1$-$C_4$-haloalkyl, halogen, nitro or cyano;

$C_3$-$C_8$-alkenyl which is unsubstituted or substituted by phenyl which in turn may be substituted by $C_1$-$C_4$-alkyl, $C_1$-$C_4$-alkoxy, $C_1$-$C_4$-haloalkyl, halogen, nitro or cyano;

$C_3$-$C_6$-haloalkenyl;

$C_3$-$C_8$-alkynyl which is unsubstituted or substituted by hydroxy or $C_1$-$C_4$-alkoxy;

$C_3$-$C_6$-cycloalkyl;

$C_5$-$C_6$-cycloalkenyl;

phenyl which is unsubstituted or substituted by $C_1$-$C_4$-alkyl, $C_1$-$C_4$-alkoxy, $C_1$-$C_4$-haloalkyl, halogen, nitro, cyano, $C_1$-$C_4$-alkoxycarbonyl or formylamino;

a 5- or 6-membered heterocyclic radical selected from the group consisting of thienyl, furyl, tetrahydrofuryl, triazolyl bonded via nitrogen, imidazolyl bonded via nitrogen, tetrahydroipyranyl, pyridyl, morpholino bonded via nitrogen, or piperidino bonded via nitrogen;

$C_6$-$C_7$-cycloalkanimino; phthalimido; succinimido; or a radical

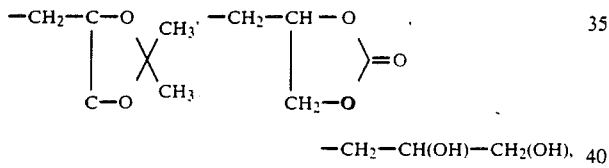

$-CH_2-CH(OH)-CH_2(OH)$, or one equivalent of a cation from the group consisting of the alkali metals, alkaline earth metals, manganese, copper, iron, ammonium and substituted ammonium;

or a radical

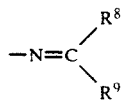

where $R^8$ and $R^9$ independently of one another are $C_1$-$C_4$-alkyl;

$C_2$-$C_6$-alkoxyalkyl; $C_3$-$C_6$-cycloalkyl; phenyl; furyl; or together form a methylene chain of the formula $-(CH_2)_m-$, where m is from 4 to 7; $R^9$ is additionally hydrogen;

$R^6$ is: hydrogen; $C_1$-$C_8$-alkyl or $C_3$-$C_8$-cycloalkyl $R^7$ is: hydrogen or $C_1$-$C_8$-alkyl, or $R^6$ and $R^7$ form a methylene chain having 4 or 5 members;

$R^3$ is: hydrogen;

$C_1$-$C_8$-alkyl which is unsubstituted or substituted by hydroxy, halogen, $C_1$-$C_4$-alkoxy, $C_1$-$C_4$-alkylthio or $C_1$-$C_4$-dialkylamino;

$C_3$-$C_8$-cycloalkyl which is unsubstituted or substituted by $C_1$-$C_4$-alkyl, halogen or $C_1$-$C_4$-haloalkyl;

$R^4$ is: hydrogen; hydroxyl; $C_1$-$C_4$-alkoxy;

$C_1$-$C_{10}$-alkyl which is unsubstituted or substituted by $C_1$-$C_4$-alkyloxy, $C_1$-$C_4$-haloalkoxy, $C_1$-$C_4$-alkylthio, $C_1$-$C_4$-dialkylamino, halogen, $C_3$-$C_6$-cycloalkyl or phenyl, which in turn may be substituted by halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$C_3$-$C_{10}$-alkenyl or $C_3$-$C_{10}$-alkynyl which is unsubstituted or substituted by halogen or $C_1$-$C_4$-alkoxy;

$C_3$-$C_8$-cycloalkyl which is unsubstituted or substituted by $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, nitro or cyano;

$C_1$-$C_4$-dialkylamino;

a 3-membered to 6-membered heterocyclic radical which is unsubstituted or substituted by $C_1$-$C_6$-alkyl, $C_1$-$C_6$-haloalkyl or halogen, said heterocyclic radical being one member selected from the group consisting of tetrahydropyranyl, tetrahydrofuryl, thiazolyl, pyridyl, pyrimidyl, morpholino bonded via nitrogen and piperidino bonded via nitrogen;

phenyl which is unsubstituted or substituted by $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, nitro, cyano, formyl, $C_1$-$C_6$-alkanoyl or $C_1$-$C_6$-haloalkanoyl;

with the proviso that $R^1$ is not $CH_3$ when $R^2$ is COOH, $COOC_2H_5$ or $CONH_2$ and $R^3$ and $R^4$ are both hydrogen;

further proviso that $R^1$ is not phenyl when $R^2$ is $COOCH_3$ and $R^3$ and $R^4$ are both hydrogen;

and their agriculturally acceptable salts.

2. Isoxazole-5-carboxamides of the formula I as set forth in claim 1, where $R^3$ is hydrogen.

3. Isoxazole-5-carboxamides of the formula I as set forth in claim 1, where $R^1$ is: hydrogen or $C_1$-$C_4$-alkyl;

$R^2$ is: $COYR^5$, where Y is oxygen or sulfur and $R^5$ is hydrogen;

$C_1$-$C_4$-alkyl; phenyl which is unsubstituted or substituted by $C_1$-$C_4$-alkyl, $C_1$-$C_4$-haloalkyl, $C_1$-$C_4$-alkoxy, $C_1$-$C_4$-alkylthio or halogen; or the radical

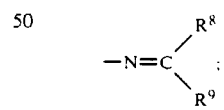

$R^3$ is hydrogen and $R^4$ is $C_1$-$C_4$-alkyl or $C_3$-$C_8$-cycloalkyl.

4. An isoxazole-5-carboxamide of the formula I as set forth in claim 1, where $R^1$ is n-propyl, $R^2$ is propan-2-iminoxycarbonyl, $R^3$ is hydrogen and $R^4$ is tert-butyl.

5. A herbicidal agent comprising an agriculturally acceptable carrier and an isoxazole-5-carboxamide of the formula I as set forth in claim 1.

6. A process for combating the growth of unwanted plants wherein said plants and/or the area to be kept free of said plants are treated with a herbicidally effective amount of an isoxazole-5-carboxamide of the formula I where

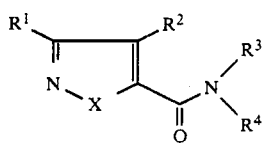

X is oxygen,
R¹ is hydrogen;
C₁–C₁₀-alkyl which is unsubstituted or substituted by C₁–C₃-alkoxy, C₁–C₃-haloalkoxy, halogen, cyano or phenyl, which in turn may be substituted by halogen, C₁–C₄-alkyl, C₁–C₄-haloalkyl, C₁–C₄-alkoxy, C₁–C₄-haloalkoxy, C₁–C₄-alkylthio, C₁–C₄-haloalkylthio, cyano, or nitro;
C₁–C₄-alkoxy;
C₃–C₈-cycloalkyl which is unsubstituted or substituted by C₁–C₄-alkyl or halogen;
phenyl which is unsubstituted or substituted by C₁–C₆-alkyl, C₁–C₆-haloalkyl, C₁–C₆-alkoxy, C₁–C₆-haloalkoxy, C₁–C₆-alkylthio, C₁–C₆-haloalkylthio, halogen, nitro or cyano;
a 5- or 6-membered heterocyclic radical which is unsubstituted or substituted by C₁–C₄-alkyl, carboxyl or C₁–C₄-alkoxycarbonyl, said heterocyclic radical being attached via carbon and selected from the group consisting of tetrahydrofuryl, tetrahydropyranyl, pyridyl, thienyl, furyl and pyrazolyl;
R² is: formyl; 4,5-dihydrooxazol-2-yl; or a radical of the formula —COYR⁵ or —CONR⁶R⁷, where
Y is oxygen or sulfur;
R⁵ is: hydrogen;
C₁–C₈-alkyl which is unsubstituted or substituted by C₁–C₄-alkoxy, C₁–C₄-alkoxy-C₁–C₄-alkoxy, halogen, cyano, hydroxy, trimethylsilyl, C₁–C₄-alkylthio, C₁–C₄-alkylamino, C₁–C₄-dialkylamino, C₁–C₄-alkylsulfinyl, C₁–C₄-alkylsulfonyl, carboxyl, C₁–C₄-alkoxycarbonyl, C₁–C₄-dialkylaminocarbonyl, C₁–C₄-dialkoxyphosphonyl, 2-propane-iminooxy, thienyl, furyl, tetrahydrofuryl, phthalimido, pyridyl, benzyloxy, benzoyl which is unsubstituted or substituted by C₁–C₄-alkyl, C₁–C₃-alkoxy or halogen; and phenyl which is unsubstituted or substituted by C₁–C₄-alkyl, C₁–C₄-alkoxy, C₁–C₄-haloalkyl, halogen, nitro or cyano;
C₃–C₈-alkenyl which is unsubstituted or substituted by phenyl which in turn may be substituted by C₁–C₄-alkyl, C₁–C₄-alkoxy, C₁–C₄-haloalkyl, halogen, nitro or cyano;
C₃–C₆-haloalkenyl;
C₃–C₈-alkynyl which is unsubstituted or substituted by hydroxy or C₁–C₄-alkoxy;
C₃–C₆-cycloalkyl;
C₅–C₆-cycloalkenyl;
phenyl which is unsubstituted or substituted by C₁–C₄-alkyl, C₁–C₄-alkoxy, C₁–C₄-haloalkyl, halogen, nitro, cyano, C₁–C₄-alkoxycarbonyl or formylamino;
a 5- or 6-membered heterocyclic radical selected from the group consisting of thienyl, furyl, tetrahydrofuryl, triazolyl bonded via nitrogen, imidazolyl bonded via nitrogen, tetrahydropyranyl, pyridyl, morpholino bonded via nitrogen, or piperidino bonded via nitrogen;
C₆–C₇-cycloalkanimino; phthalimido; succinimido; or a radical

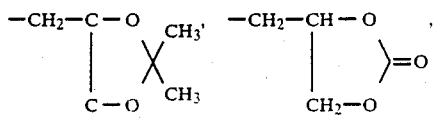

—CH₂—CH(OH)—CH₂(OH), or one equivalent of a cation from the group consisting of the alkali metals, alkaline earth metals, manganese, copper, iron, ammonium and substituted ammonium;
or a radical

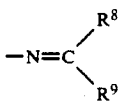

where R⁸ and R⁹ independently of one another are C₁–C₄-alkyl;
C₂–C₆-alkoxyalkyl; C₃–C₆-cycloalkyl; phenyl; furyl; or together form a methylene chain of the formula —(CH₂)ₘ—, where m is from 4 to 7; R⁹ is additionally hydrogen;
R⁶ is: hydrogen; C₁–C₈-alkyl or C₃–C₈-cycloalkyl
R⁷ is: hydrogen or C₁–C₈-alkyl, or
R⁶ and R⁷ form a methylene chain having 4 or 5 members;
R³ is: hydrogen;
C₁–C₈-alkyl which is unsubstituted or substituted by hydroxy, halogen, C₁–C₄-alkoxy, C₁–C₄-alkylthio or C₁–C₄-dialkylamino;
C₃–C₈-cycloalkyl which is unsubstituted or substituted by C₁–C₄-alkyl, halogen or C₁–C₄-haloalkyl;
R⁴ is: hydrogen; hydroxyl; C₁–C₄-alkoxy;
C₁–C₁₀-alkyl which is unsubstituted or substituted by C₁–C₄-alkyloxy, C₁–C₄-haloalkoxy, C₁–C₄-alkylthio, C₁–C₄-dialkylamino, halogen, C₃–C₆-cycloalkyl or phenyl, which in turn may be substituted by halogen, cyano, nitro, C₁–C₄-alkyl, C₁–C₄-haloalkyl, C₁–C₄-alkoxy, C₁–C₄-haloalkoxy, C₁–C₄-alkylthio or C₁–C₄-haloalkylthio;
C₃–C₁₀-alkenyl or C₃–C₁₀-alkynyl which is unsubstituted or substituted by halogen or C₁–C₄-alkoxy;
C₃–C₈-cycloalkyl which is unsubstituted or substituted by C₁–C₆-alkyl, C₁–C₆-haloalkyl, C₁–C₆-alkoxy, C₁–C₆-haloalkoxy, C₁–C₆-alkylthio, C₁–C₆-haloalkylthio, halogen, nitro or cyano;
C₁–C₄-dialkylamino;
a 3-membered to 6-membered heterocyclic radical which is unsubstituted or substituted by C₁–C₆-alkyl, C₁–C₆-haloalkyl or halogen, said heterocyclic radical being one member selected from the group consisting of tetrahydropyranyl, tetrahydrofuryl, thiazolyl, pyridyl, pyrimidyl, morpholino bonded via nitrogen and piperidino bonded via nitrogen;
phenyl which is unsubstituted or substituted by C₁–C₆-alkyl, C₁–C₆-haloalkyl, C₁–C₆-alkoxy, C₁–C₆-haloalkoxy, C₁–C₆-alkylthio, C₁–C₆-haloalkylthio, halogen, nitro, cyano, formyl, C₁–C₆-alkanoyl or C₁–C₆-haloalkanoyl;
and their agriculturally acceptable salts.

* * * * *